US009678045B2

(12) United States Patent
Zhu et al.

(10) Patent No.: US 9,678,045 B2
(45) Date of Patent: Jun. 13, 2017

(54) DEVICES, SYSTEMS, AND METHODS FOR NON-DESTRUCTIVE TESTING OF MATERIALS AND STRUCTURES

(71) Applicant: Board of Regents, The University Of Texas System, Austin, TX (US)

(72) Inventors: Jinying Zhu, Round Rock, TX (US); Michael R. Haberman, Austin, TX (US); Xiaowei Dai, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 627 days.

(21) Appl. No.: 14/014,877

(22) Filed: Aug. 30, 2013

(65) Prior Publication Data

US 2014/0060193 A1 Mar. 6, 2014

Related U.S. Application Data

(60) Provisional application No. 61/695,539, filed on Aug. 31, 2012.

(51) Int. Cl.
*G10K 11/28* (2006.01)
*G10K 15/06* (2006.01)
*G01N 29/24* (2006.01)
*G01N 29/34* (2006.01)

(52) U.S. Cl.
CPC ......... *G01N 29/34* (2013.01); *G01N 29/2431* (2013.01); *G01N 29/2456* (2013.01); *G10K 11/28* (2013.01); *G10K 15/06* (2013.01)

(58) Field of Classification Search
CPC .............. G01N 29/34; G01N 29/2431; G01N 29/2456; G10K 11/28; G10K 15/06

USPC ........................................................... 73/596
See application file for complete search history.

(56) References Cited

U.S. PATENT DOCUMENTS

| | | | | |
|---|---|---|---|---|
| 2,643,727 | A | * 6/1953 | Leon | H04R 1/345 181/155 |
| 4,907,671 | A | * 3/1990 | Wiley | H04R 1/345 181/155 |
| 5,072,733 | A | 12/1991 | Spector et al. | |
| 5,399,146 | A | 3/1995 | Nowacki et al. | |
| 5,616,865 | A | 4/1997 | Webster | |

(Continued)

FOREIGN PATENT DOCUMENTS

| | | | |
|---|---|---|---|
| GB | 2468547 | * 9/2010 | G21F 9/00 |
| GB | 2468546 | * 9/2016 | |
| JP | 2005/084036 | 3/2005 | |

OTHER PUBLICATIONS

Chretien, N., "Stress wave propagation from electrical discharge on cylindrical aluminum rod," Ultrasonics, vol. 16, No. 2, 1978, pp. 69-76.

(Continued)

*Primary Examiner* — J M Saint Surin
(74) *Attorney, Agent, or Firm* — Meunier Carling & Curfman LLC

(57) ABSTRACT

Provided are devices, systems, and methods for the testing of materials and structures. For example, the devices, systems, and methods are optionally used for the non-destructive testing of a material or structure. Furthermore, the devices, systems, and methods may optionally use a high-amplitude, air-coupled acoustic source for non-destructive testing of materials and structures.

38 Claims, 19 Drawing Sheets

(56) References Cited

U.S. PATENT DOCUMENTS

| | | | | |
|---|---|---|---|---|
| 5,824,908 | A | * | 10/1998 | Schindel ............... G01N 29/11 73/598 |
| 6,068,080 | A | * | 5/2000 | LaCarrubba ............ H04R 1/34 181/155 |
| 6,820,718 | B2 | * | 11/2004 | LaCarrubba ........... H04R 1/345 181/155 |
| 7,791,253 | B2 | | 9/2010 | Bhardwaj |
| 2006/0225509 | A1 | * | 10/2006 | Haupt ..................... F41H 11/12 73/649 |
| 2008/0078249 | A1 | | 4/2008 | May |

OTHER PUBLICATIONS

Cooper, J.A., et al., "High-voltage spark discharge source as an ultrasonic generator," IEE Proceedings A Physical Science, Measurement and Instrumentation, Management and Education, Reviews, vol. 131, No. 4, 1984, p. 275.

Cornwell, M.A., et al., "Laser ultrasonics in copy paper: Bending stiffness dependence on temperature and moisture content," The Journal of the Acoustical Society of America, vol. 112, No. 6, 2002, p. 2763.

Dai, Xiaowei, et al., "A focused electric spark source for non-contact stress wave excitation in solids," Journal of the Acoustical Society of America, vol. 134, No. 6, Dec. 2013, pp. EL513-EL519.

Dai, Xiaowei et al., "Use of parabolic reflector to amplify in-air signals generated during impact-echo testing," J. Acoust. Soc. Am., vol. 130, No. 4, Oct. 2011, pp. EL167-EL172.

Ealo, J.L., et al., "Airborne ultrasonic phased arrays using ferroelectrets: a new fabrication approach," IEEE transactions on ultrasonics, ferroelectrics, and frequency control, vol. 56, No. 4, Apr. 2009, pp. 848-858.

Gachagan, A., et al., "Characterization of air-coupled transducers," IEEE Transactions on Ultrasonics, Ferroelectrics and Frequency Control, vol. 43, No. 4, Jul. 1996, pp. 678-689.

Gibson, A., et al., "Lamb Wave Basis for Impact-Echo Method Analysis," J. Eng. Mech., vol. 131, No. 4, 2005, pp. 438-443.

Hamilton, M.F., Transient axial solution for the reflection of a spherical wave from a concave ellipsoidal mirror, The Journal of the Acoustical Society of America, vol. 93, No. 3, 1993, p. 1256.

Hosten, B., "Measurement of elastic constants in composite materials using air-coupled ultrasonic bulk waves," The Journal of the Acoustical Society of America, vol. 99, No. 4, 1996, p. 2116.

Korolev, S.V., et al., "Efficient excitation of Rayleigh waves by a strong shock wave initiated by a spark in air," Sov Tech. Phys. Lett., vol. 14, No. 11, Nov. 1988, pp. 843-845.

Kuznetsov, V.P., "Equations of nonlinear acoustics," Sov. Phys. Acoust, vol. 16, 1970, pp. 467-470.

Prada, Claire, et al., "Power law decay of zero group velocity Lamb modes," Wave Motion, vol. 45, 2008, pp. 723-728.

Sansalone, Mary, "Impact-Echo: The Complete Story," ACI Structural Journal, Nov.-Dec. 1997, pp. 777-786.

Wright, W.M., "Propagation in air of N waves produced by sparks," The Journal of the Acoustical Society of America, vol. 73, No. 6, 1983, p. 1948.

Wright, W.M., et al., "Focusing of N waves in air by an ellipsoidal reflector," The Journal of the Acoustical Society of America, vol. 102, No. 2, Aug. 1997, p. 741.

Yu, T.-Y., et al., "Damage inspection of fiber reinforced polymer-concrete systems using a distant acoustic-laser NDE technique," Proceedings of SPIE, vol. 7649, 2010, pp. 76491J-1 through 76491J-8.

Zabolotskaya, E.A., et al., "Quasi-plane waves in the nonlinear acoustics of confined beams," Sov. Phys. Acoust., vol. 15, 1969, pp. 35-40.

Zhu, Jinying, et al., "Imaging Concrete Structures Using Air-Coupled Impact-Echo," Journal of Engineering Mechanics, vol. 133, No. 6, 2007, pp. 628-640.

Zhu, Jinying, et al., "Leaky Rayleigh and Scholte waves at the fluid-solid interface subjected to transient point loading," The Journal of the Acoustical Society of America, vol. 116, No. 4, 2004, p. 2101.

Zhu, Jinying, et al., "Non-contact imaging for surface-opening cracks in concrete with air-coupled sensors," Materials and Structures/Materiaux et Constructions, vol. 38, No. 283, 2005, pp. 801-806.

International Preliminary Report on Patentability, issued on Mar. 3, 2015, in connection with corresponding International Application No. PCT/US2013/056146.

International Search Report and Written Opinion, dated Feb. 17, 2014, in connection with corresponding International Application No. PCT/US2013/056146.

* cited by examiner

DEVICES, SYSTEMS, AND METHODS FOR NON-DESTRUCTIVE TESTING OF MATERIALS AND STRUCTURES

CROSS-REFERENCE TO RELATED APPLICATIONS

This application claims the benefit of U.S. Provisional Patent Application No. 61/695,539, filed Aug. 31, 2012, which is incorporated herein by reference in its entirety.

STATEMENT REGARDING FEDERALLY SPONSORED RESEARCH

This invention was made with government support under Grant No. 70NANB10H014 awarded by the United States Department of Commerce/National Institutes of Standards and Technology. The Government has certain rights in the invention.

FIELD OF THE INVENTION

The present disclosure relates generally to devices, systems and methods for non-destructive testing of materials and structures.

BACKGROUND

Various structures, buildings, and bridges across the United States and around the world require testing and evaluation of the integrity of various structural components. This testing and evaluation can assist governmental entities, companies, and other entities with the allocation of funds and resources for repair, demolition, or reconstruction of these structures.

For example, in the U.S., the Federal Highway Administration estimated in 2010 that approximately one-quarter of the bridges in the U.S. were structurally deficient. The estimated annual maintenance cost for such structures is in excess of $70 billion. In the cases of many bridges in the U.S., the bridge decks must be replaced and/or repaired once structural integrity is comprised. Furthermore, the American Society of Civil Engineers assigned the U.S. the letter "D+" in 2013 for its infrastructure, concluding that infrastructure of the U.S. is deteriorating.

The monitoring of the structural integrity of buildings, bridges, and other structures is essential for public safety. Where buildings fall into disrepair, or the materials or structural components of the building lose structural integrity, the buildings and any relevant components of that building must be replaced, repaired, or other appropriate action taken. The same is true of bridges and other structures. Where structural issues are not addressed, the public is at risk, as well as other entities, such as for example insurance companies, for any injuries, death, or other damage that may result from these structures.

The evaluation of the damage to a material or change in a mechanical property of a material may not, in some instances, be visible on the exterior portion of the structure. The internal changes in one or more mechanical properties and internal damage of a material may require the use of devices or systems for the evaluation of the internal properties of a material.

Aside from structures, bridges, and other infrastructure, companies and other businesses are likewise concerned in regards to the quality of their products and public safety when using their products. Therefore, these entities regularly monitor the quality control of their processes and products, in order to ensure a certain level of quality and structural and mechanical integrity.

SUMMARY

Provided are devices, systems, and methods for the testing of materials and structures. For example, the devices, systems, and methods are optionally used for the non-destructive testing of a material or structure. Furthermore, the devices, systems, and methods may optionally use a high-amplitude, air-coupled acoustic source for non-destructive testing of materials and structures.

An example acoustic source for non-destructive testing of a material includes a sound generator. The acoustic source further includes a focusing apparatus. The focusing apparatus focuses sound generated through air and onto a surface of the material to create wave motion within the material. For example, the source may be used on material, which includes porous concrete, concrete, metal, and composite materials.

The sound generator may produce sound with energy in frequencies sufficient for excitation of wave motion in the material. The sound generator optionally produces sound with a peak sound pressure level sufficient to penetrate into the material. The peak sound pressure level may be between about 120 dB and 185 dB re 20 microPa.

Furthermore, the sound generator optionally produces an electrical spark which generates the sound. The sound generator may also include two electrodes spaced from one another by a predetermined gap distance. The gap distance may be between about 0.1 mm and 10 mm. In order to produce the sound, a spark may be generated between the two electrodes. The discharge voltage may be between about 1 kV and 30 kV.

The focusing apparatus optionally reflects sound produced by the sound generator. The focusing apparatus optionally includes an ellipsoidal sound reflector. For example, the sound generator may produce an electrical spark at one focus of the ellipsoidal sound reflector to generate the sound. The ellipsoidal sound reflector optionally has an ellipsoidal reflector eccentricity of about 0-1. The ellipsoidal sound reflector may have an ellipsoidal reflector depth of about 5-300 mm. The ellipsoidal sound reflector may also have an ellipsoidal reflector minor axis of about 5-300 mm.

The acoustic source may optionally produce sound having an amplitude at the focus that is focused on a localized portion of the surface of the material. For example, the amplitude at the focus may be between about 0.5 kPa and 30 kPa. The amplitude at the focus may optionally be between about 1 kPa and 5 kPa. Furthermore, the amplitude at the focus may be between about 5 kPa and 10 kPa. The duration of the sound is optionally between about 0.5 microseconds and 1 millisecond.

The frequency of the sound focused on the material is optionally between about 1-100 kHz. The frequency of the sound focused on the material may also be between about 100-500 kHz. The frequency of the sound focused on the material is optionally between about 0.5-2.0 MHz.

Also provided in the current disclosure is an example method for non-destructive testing of a material. The method includes generating a sound with an acoustic source. The method further includes focusing the generated sound on the surface of the material through the air. At least a portion of the acoustic source is optionally in contact with the surface. Alternatively, the acoustic source may be spaced a distance from the surface of the material. For example, the distance is optionally at least about 1.0 mm from the surface of the material. Optionally, the distance is between about 1.0 mm and about 20 cm from the surface of the material. The distance may also be between about 1 cm and 20 cm from the surface of the material. Optionally, the distance is between about 5 cm and about 20 cm from the surface of the material. The distance may also be between about 1 mm and 1 cm from the surface of the material. Optionally, the distance is between about 1 cm and about 5 cm from the surface of the material.

The method optionally includes receiving sound produced from wave motion within the material. Furthermore, the method may include processing the received sound to evaluate the material. The evaluation optionally includes determining whether there is damage or a mechanical property change within the material.

Also provided is an example method for non-destructive testing of a material. The example method includes generating a sound and transmitting the generated sound. The transmitted sound is then coupled through air into a material to cause wave motion within the material. The method further includes receiving sound from the material resulting from the wave motion, and the received sound is used to evaluate the material.

The coupled sound optionally penetrates into the material to a depth of about 1-25 mm. The coupled sound may penetrate into the material to a depth of about 25-250 mm. Optionally, the coupled sound may penetrate into the material to a depth of about 250-625 mm.

The method may also include focusing the sound onto the surface of the material. For example, the sound has energy in frequencies sufficient for excitation of wave motion in the material. The sound optionally has a power sufficient to penetrate into the material. The sound may be produced by a sound generator that produces an electrical spark which generates the sound. The sound generator optionally includes two electrodes spaced from one another by a predetermined gap distance. For example, the gap distance may be between about 0.1 mm and 10 mm. A spark may be generated between the two electrodes to produce sound. The discharge voltage is optionally between about 1 and 30 kV.

The focusing may be accomplished with the use of a focusing apparatus. The focusing apparatus optionally reflects sound onto a region of the surface of the material. The focusing apparatus optionally includes an ellipsoidal sound reflector. For example, the sound generator may produce an electrical spark at one focus of the ellipsoidal sound reflector to generate the sound. The ellipsoidal sound reflector optionally has an ellipsoidal reflector eccentricity of about 0-1. The ellipsoidal sound reflector may have an ellipsoidal reflector depth of about 5-300 mm, and optionally has an ellipsoidal reflector minor axis of about 5-300 mm.

The sound produced optionally has an amplitude at the focus that is focused on a localized portion of the surface of the material. The duration of the sound is optionally between about 0.5 microseconds and 1 millisecond. The frequency of the sound focused on the material is optionally between about 1-100 kHz. The frequency of the sound focused on the material may also be between about 100-500 kHz. The frequency of the sound focused on the material is optionally between about 0.5-2.0 MHz. The example method may be performed on material, including a porous aggregate, concrete, and metal.

The example method may further include the repetition of generating sound, and transmitting the generated sound. Furthermore, the example method may include the repetition of coupling the transmitted sound through air into a material to generate wave motion within the material. Also, the example method may further include receiving sound from the material resulting from the wave motion to evaluate the material. The received sound from a plurality of generation and transmission events may be averaged to evaluate the material.

Also provided herein is a system for non-destructive testing of a material. The system includes an acoustic source and a receiver for receiving sound produced from the wave motion of the material. For example, the receiver may optionally be spaced from the source and spaced from the material. The receiver is optionally a microphone. The system may further include at least one processor configured to process the received sound to evaluate the material. For example, the processing of the sound includes evaluation of whether the material is damaged or has mechanical property changes.

These and other features and advantages of the implementations of the present disclosure will become more readily apparent to those skilled in the art upon consideration of the following detailed description and accompanying drawings, which describe both the preferred and alternative implementations of the present disclosure.

BRIEF DESCRIPTION OF THE DRAWINGS

In the drawings, like reference numbers and designations in the various drawings indicate like elements.

DETAILED DESCRIPTION

Figure 1A:
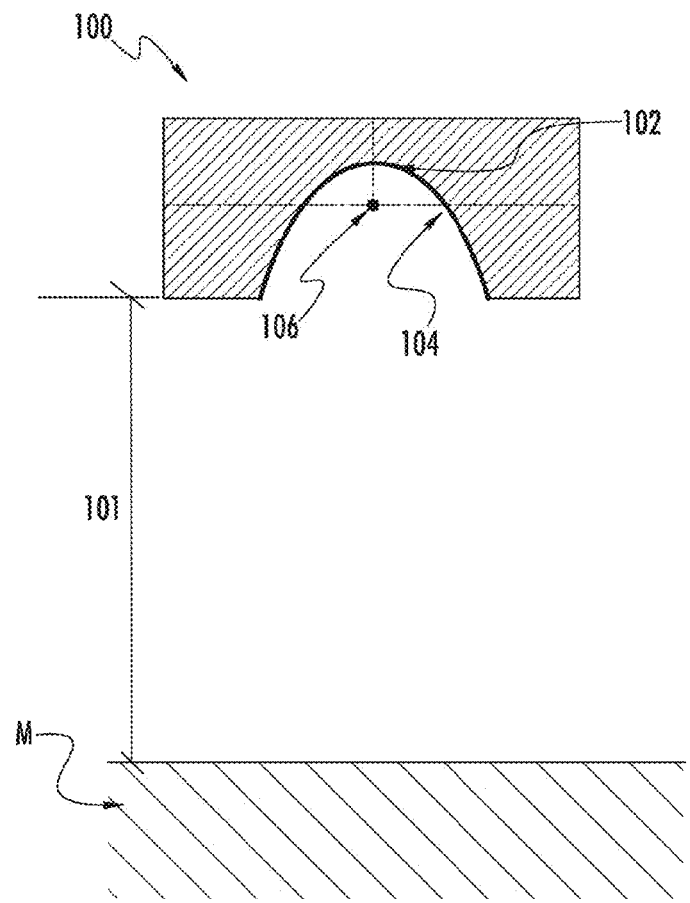
FIGS. 1A and 1B are schematic illustrations showing example acoustic sources for non-destructive testing of a material.

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a," "an," and "the," include plural referents unless the context clearly indicates otherwise.

Non-destructive testing (NDT) has become a widely used solution for numerous types of industrial projects in the manufacturing, construction, plant operation and other engineering sectors. Using NDT test methods, devices and systems, it is possible to examine an object, material or system without impairing its future usefulness. NDT is often required to verify the quality of a product or system. Some commonly used NDT techniques include, for example, acoustic emission testing, acoustic resonance testing, electromagnetic testing, infrared testing, leak testing, magnetic particle testing, dye penetrant testing, dye penetrant testing, radiographic testing, ultrasonic testing, and visual testing or inspection, among others.

By using NDT, visual examination is no longer the principal means of determining quality. NDT techniques are used worldwide to detect variations in structure, minute changes in surface finish, and the presence of cracks or other physical discontinuities. Moreover, NDT methods are used to measure the thickness of materials and coatings, and to determine other characteristics of industrial products.

NDT may be used not only for industrial machines and various components of systems, but also for structural components. One such structural component, for example, includes concrete. In the concrete arena, it is often necessary to test concrete structures after the concrete has hardened to determine whether the structure is suitable for its designed use. The testing should ideally be performed without destruction or damage to the concrete. The range of properties that can be assessed using NDT is quite large and includes fundamental parameters, such as density, elastic modulus, and strength, as well as surface hardness, surface absorption, and the size and distance of reinforcement from the surface of the material. In other cases, NDT may provide feedback regarding the quality of workmanship and structural integrity by the ability to detect voids, cracking, and delamination. Delamination is also a mode of failure for many composite materials.

NDT may be applied to both new and old structures. For new structures, the principal applications are likely to be for quality control or the assessment of the quality of materials or construction. On the other hand, the testing of existing structures is usually related to an assessment of structural integrity or adequacy, as would be the case with an older bridge, for example.

As previously mentioned, ultrasonic testing is a widely used NDT technique for defect detection, thickness measurement and material property characterization of bridges, buildings, and other structures. In traditional ultrasonic testing, piezoelectric transducers are used to generate and detect ultrasonic waves in materials. This type of ultrasonic testing involves contact of the detective device or apparatus with the surface of the material or immersion of parts to be tested in a fluid, such as water, for non-contact testing. Testing speed and repeatability using contact-type piezoelectric transducers is limited by the coupling requirement between the transducers and the material surface. Furthermore, the coupling quality is problematic for porous or rough materials, such as composites and concrete. Further, immersion techniques are not possible on many large parts or parts that can absorb or be deteriorated by water.

Figure 7A:
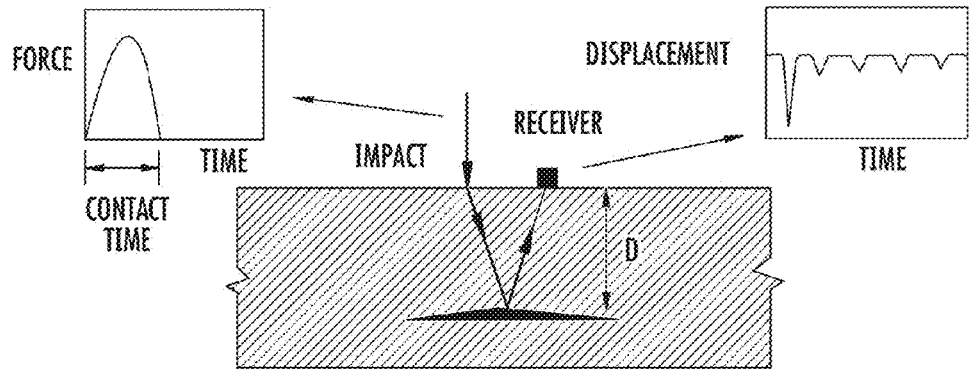
FIG. 7A is a schematic illustration showing an example setup for impact-echo testing.
Figures 7B, 7C:
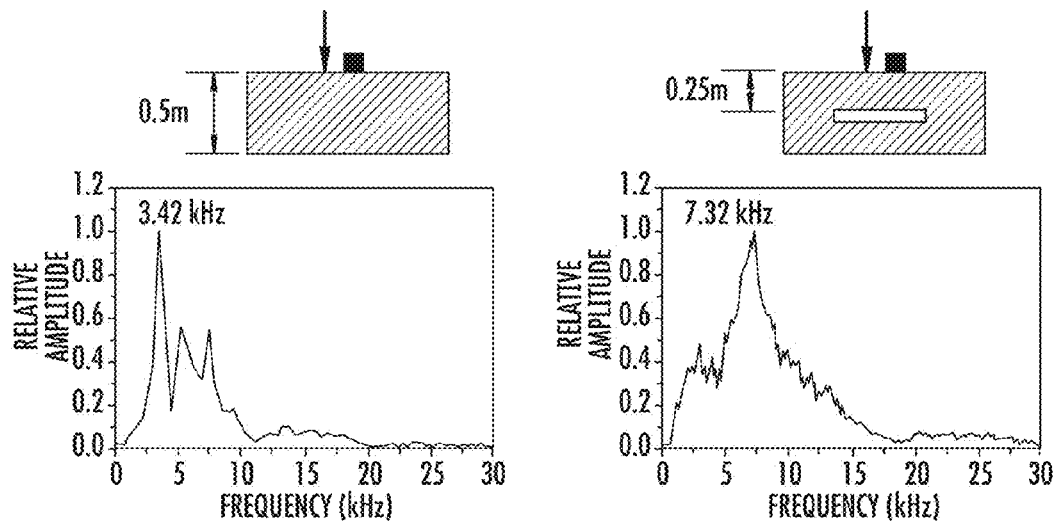
FIGS. 7B and 7C are graphs showing results from impact-echo testing.

The impact-echo test is a commonly used NDT method to determine concrete thickness and locate delaminations. Under this method, an impact, imparted by something such as a hammer, is made on the surface of the material, and a receiver measures the amplitude of the resulting wave motion on the surface. Referring to FIG. 7, an example setup for impact-echo testing and results from the test are shown. The depth, represented by D in FIG. 7, may be represented as follows:

$$D = \beta \frac{C_p}{2f}$$

The β may be from approximately 0.6 to 0.975. A typical value of β may be approximately 0.96 for concrete.

Over the years, NDT technologies have emerged for non-contact ultrasonic wave excitation and sensing. For example, these technologies include laser ultrasonic, air-coupled acoustic sensing, and electromagnetic-acoustic transducers (EMAT). One drawback to EMAT is that these transducers can only be applied to conductive materials or materials having a thin, conductive cover layer. Ultrasound generation by laser, for example, is based on the principle of thermal expansion or ablation of the test material using a short duration illumination of the material surface with a high energy laser. These and other ultrasonic systems, however, require expensive equipment and a stable platform for equipment monitoring. Further, the frequency range of laser induced ultrasound is often too high for many heterogeneous materials, such as for example concrete, and the damage induced if ablation occurs is often not acceptable. The current systems are also problematic in the sense that they require a high power to operate and are very inefficient transduction mechanisms.

The performance of air-coupled sensors has also been improved over the years and their applications broadened. Although air-coupled sensors are currently used for NDT of composite materials, there exists a high acoustic impedance mismatch between air and materials of interest. This mismatch presents a challenge to the implementation of a fully air-coupled NDT system to materials with high acoustic impedance and thick structural members. Furthermore, despite the fact that piezopolymers, ferroelectrets, and capacitive sources are well coupled to air, they are only capable of providing limited source level and can require thousands of averages to attain a single measurement.

Currently available systems, devices, and methods are large and bulky and do not allow NDT for a wide variety of materials. Furthermore, many of these systems, devices, and methods require contact between the detective device or apparatus and the surface of the material.

The systems, devices, and methods disclosed herein provide for the non-destructive testing of a material. Furthermore, the present disclosure eliminates the need for fluid-coupled non-destructive testing of a material, or non-destructive testing of material that requires very large devices. The present disclosure also provides for the evaluation of damage or a mechanical change within a material through non-contact and acoustic technology. The system, methods, and devices disclosed herein provide air-coupled sources for non-destructive testing of a material. The systems, methods, and devices disclosed herein are also used to achieve efficient generation of high amplitude acoustic waves for evaluation of high impedance solids and materials. The present disclosure provides air-coupled sensing for an efficient and accurate NDT system.

Referring to FIG. 1A, an example acoustic source 100 for non-destructive testing of a material is shown. The example acoustic source 100 for non-destructive testing of a material M includes a sound generator 102. The acoustic source 100 further includes a focusing apparatus 104. The focusing apparatus 104 focuses sound generated through air and onto a surface of the material M to create wave motion within the material M.

For example, the source 100 may be used on material M, which includes porous concrete, concrete, metal, and composite materials. For example, testing may be performed on concrete for depths up to at least about 625 mm. In addition, the source 100 may optionally be used on high impedance materials, including for example metals, composite materials, and other construction materials. The source 100 may also be used in many industries, including for example infrastructure, aerospace, materials fabrication, automotive, and petrochemical. Furthermore, the source 100 may optionally be utilized for periodic monitoring of the viability of structures, rough surface characterization, corrosion monitoring, the stiffness, and the loss properties of composite materials.

The source 100 may be used in a variety of industries and for a variety of purposes, and is advantageous, for example, for its provisions of higher amplitude and broader bandwidth. For example, the sound generator 102 may produce sound with energy in frequencies sufficient for excitation of wave motion in the material M. The sound generator optionally produces sound with a peak sound pressure level sufficient to penetrate into the material M. The peak sound pressure level may be between about 120 dB and 185 dB re 20 microPa. Furthermore, the sound generator 102 optionally produces an electrical spark 106 which generates the sound. The principal components and dimensions of the electrical spark 106 may be altered to adapt to the excitation of wave motion in concrete structures, as well as other materials, such as for example materials with high acoustic impedance that may require signals with higher frequency spectral content.

Figure 1B:
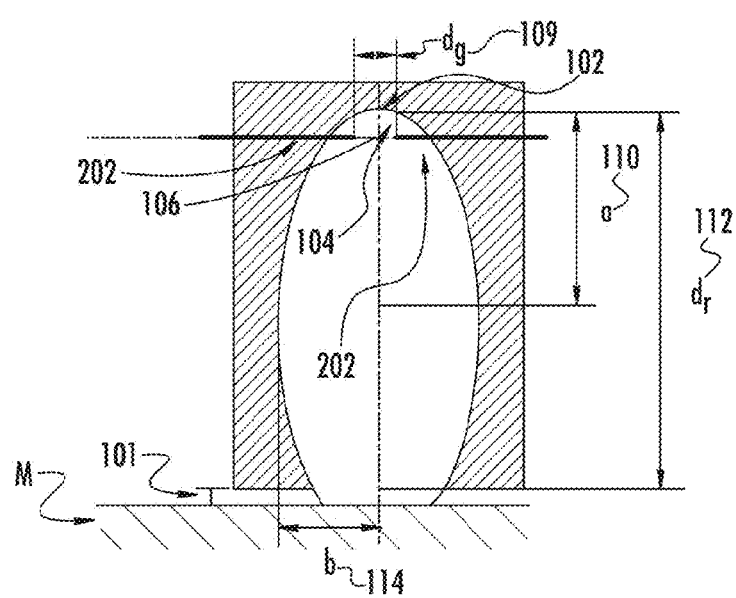
Figure 2:
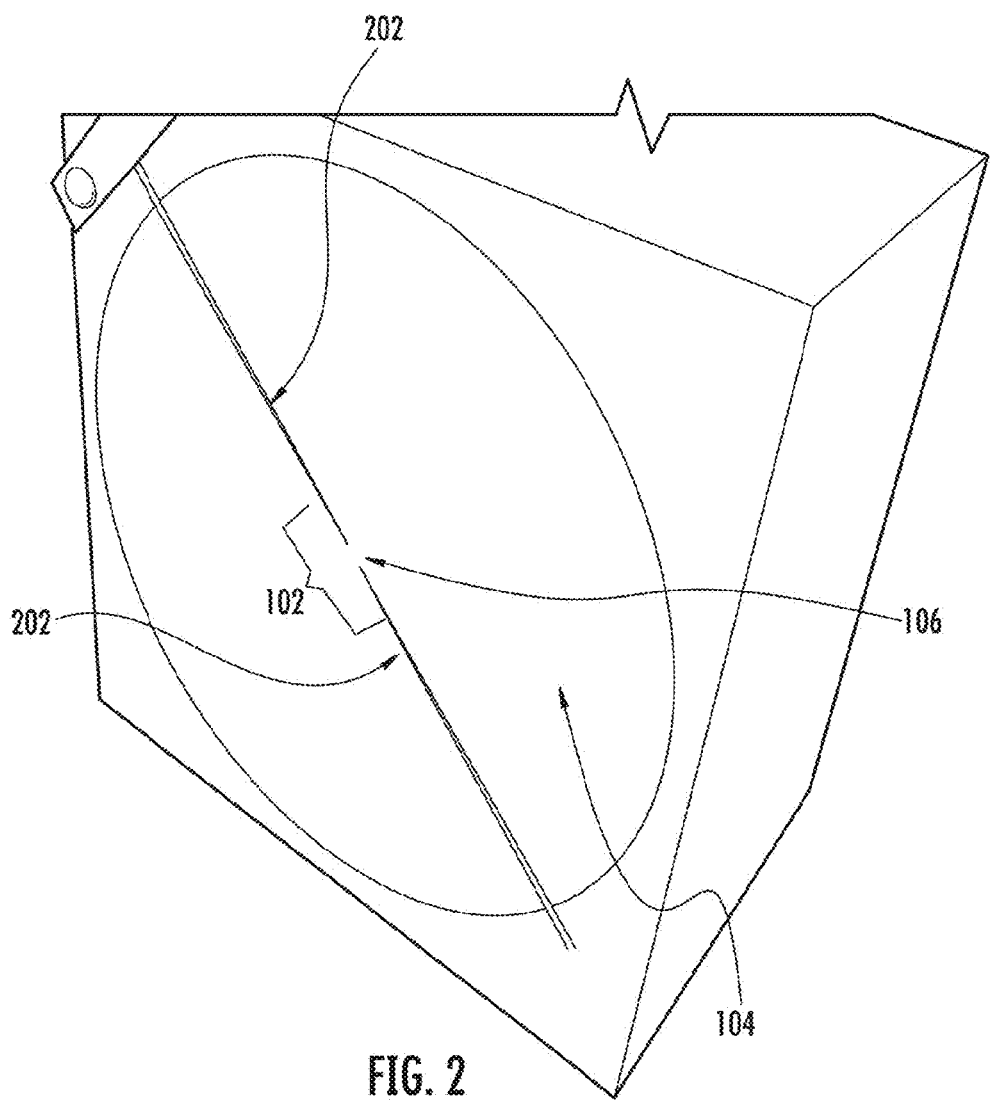
FIG. 2 is a schematic illustration of an example acoustic source.

Referring now to FIGS. 1B and 2, example acoustic sources are shown. The sound generator 102 may also include two electrodes 202 spaced from one another by a predetermined gap distance 109. The gap distance 109 may be between about 0.1 mm and 10 mm. In order to produce the sound, a spark 106 may be generated between the two electrodes 202. The discharge voltage may be between about 1 kV and 30 kV. The focusing apparatus 104 optionally reflects sound produced by the sound generator 102.

The electrical spark 106 may be produced by a trigger circuit feeding a charge into a high voltage capacitor circuit once the trigger circuit is activated. Once a breakdown voltage is achieved, the capacitor may discharge, thereby creating a spark. The electrical spark 106 may excite both impact-echo and surface wave signals. The electrical spark may be generated by an acoustic signal. The acoustic signal generated electrical spark 106 may be focused on the surface on the solid and may excite both impact-echo and surface wave signals. Furthermore, the amplitude and duration of the electrical spark 106 may be altered or changed as appropriate for field and laboratory settings, or as appropriate for the materials being tested.

Figure 3:
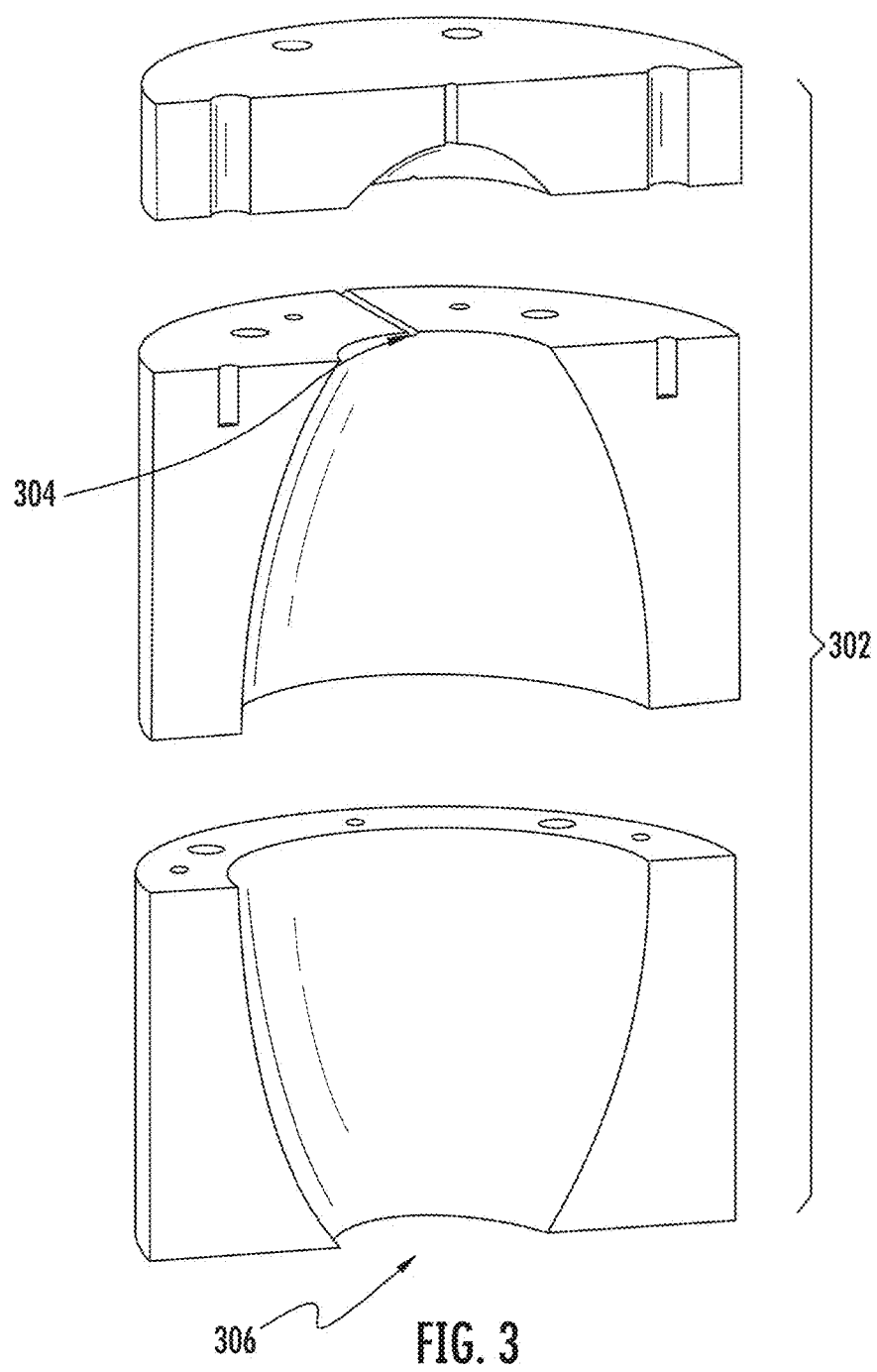
FIG. 3 is a schematic illustration of an example acoustic source.

The focusing apparatus 104 optionally includes an ellipsoidal sound reflector 302, as shown in the example acoustic source in FIG. 3. The ellipsoidal sound reflector 302 may include any material with a large impedance as compared to air, including for example metal, aluminum, steel, hard plastic materials, polycarbonate, polyphenylsulfone (PPSF or PPSU), and poly(methyl methacrylate) (PMMA), among others. For example, the sound generator 102 may produce an electrical spark 106 at one focus 304 of the ellipsoidal sound reflector 302 to generate the sound. The ellipsoidal sound reflector 302 optionally has an ellipsoidal reflector eccentricity of about 0-1. The ellipsoidal reflector eccentricity (r) may be represented as follows:

$$\epsilon = \sqrt{1-(b/a)^2}$$

where a and b are the lengths of the major and minor axes, respectively, of the ellipsoidal reflector.

The ellipsoidal sound reflector 302 may have an ellipsoidal reflector depth 112 of about 5-300 mm. A deep ellipsoidal reflector 302 may provide lower noise. The ellipsoidal sound reflector may also have an ellipsoidal reflector minor axis 110 of about 5-300 mm. The dimensions of the ellipsoidal sound reflector 302 may be reduced or altered as appropriate for various field and laboratory environments, or as may be appropriate for various materials.

An example acoustic source may optionally produce sound having an amplitude at the focus that is focused on a localized portion of the surface of the material M. For example, the amplitude at the focus may be between about 0.5 kPa and 30 kPa. The amplitude at the focus may optionally be between about 1 kPa and 5 kPa. Furthermore, the amplitude at the focus may be between about 5 kPa and 10 kPa. The duration of the sound is optionally between about 0.5 microseconds and 1 millisecond.

The frequency of the sound focused on the material M is optionally between about 1-100 kHz. The frequency of the sound focused on the material M may also be between about 100-500 kHz, such as for thick composites and metals. The frequency of the sound focused on the material M is optionally between about 0.5-2.0 MHz, such as for thin composites and metals.

Figure 5:
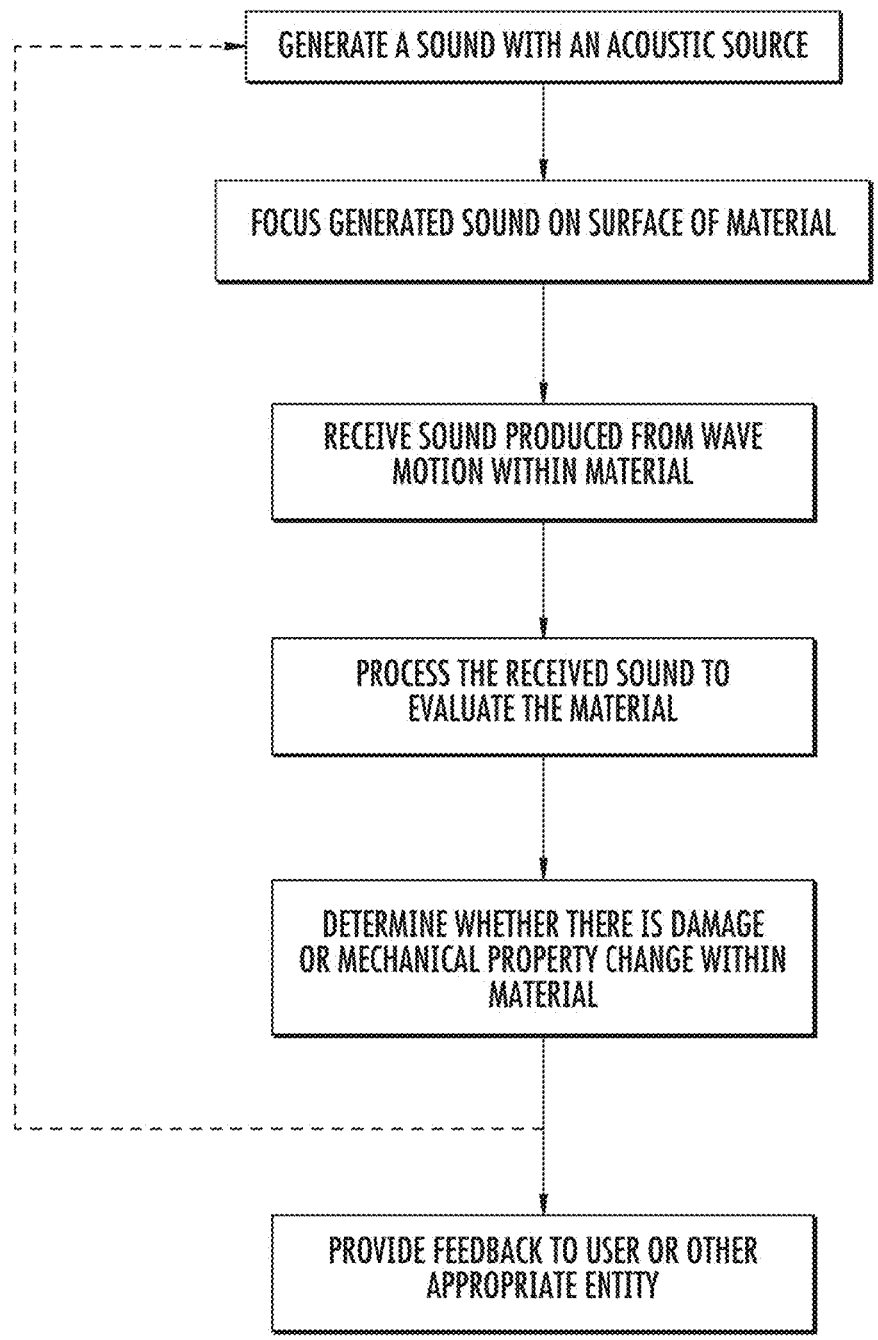
FIG. 5 is a flowchart showing an example process for non-destructive testing of a material.

Also provided in the current disclosure is an example method for non-destructive testing of a material M. Referring to FIG. 5, an example method for non-destructive testing of a material is shown. The method includes generating a sound with an acoustic source, as described above and herein. The method further includes focusing the generated sound on the surface of the material M through the air. At least a portion of the acoustic source is optionally in contact with the surface of the material M. Alternatively, the acoustic source may be spaced a distance 101 from the surface of the material M. For example, the distance 101 is optionally at least about 1.0 mm from the surface of the material M. Optionally, the distance 101 is between about 1.0 mm and about 20 cm from the surface of the material M. The distance 101 may also be between about 1 cm and 20 cm from the surface of the material M. Optionally, the distance 101 is between about 5 cm and about 20 cm from the surface of the material M. The distance 101 may also be between about 1 mm and 1 cm from the surface of the material M. Optionally, the distance 101 is between about 1 cm and about 5 cm from the surface of the material M.

The method optionally includes receiving sound produced from wave motion within the material M. Furthermore, the method may include processing the received sound to evaluate the material M. The evaluation optionally includes determining whether there is damage or a mechanical property change within the material M. The processing of the received sound may include an analysis of the sound waves produced within the material. Based on this analysis of the sound waves, the material may be evaluated to determine whether there is damage or a mechanical property change. For example, where there is internal damage to a material, the sound waves produced will vary from the sound waves produced for a material without internal damage. Thus, the researcher or other structural engineer or professional may be informed of this damage or mechanical property change through non-destructive testing of the material.

Also provided is an example method for non-destructive testing of a material M. The example method includes generating a sound and transmitting the generated sound. The transmitted sound is then coupled through air into a material to cause wave motion within the material. The method further includes receiving sound from the material M resulting from the wave motion, and the received sound is used to evaluate the material M.

The coupled sound optionally penetrates into the material M to a depth of about 1-25 mm, for materials such as, for example metals and composites. The coupled sound may penetrate into the material M to a depth of about 25-250 mm, for materials such as, for example concrete. Optionally, the coupled sound may penetrate into the material M to a depth of about 250-625 mm, for materials such as, for example concrete.

The method may also include focusing the sound onto the surface of the material M. For example, the sound has energy in frequencies sufficient for excitation of wave motion in the material M. The sound optionally has a power sufficient to penetrate into the material M. The sound may be produced by a sound generator 102 that produces an electrical spark 106 which generates the sound. The sound generator 102 optionally includes two electrodes 202 spaced from one another by a predetermined gap distance 109. For example, the gap distance 109 may be between about 0.1 mm and 10 mm. A spark 106 may be generated between the two electrodes 202 to produce sound. The discharge voltage is optionally between about 1 and 30 kV.

The focusing may be accomplished with the use of a focusing apparatus 104. The focusing apparatus 104 optionally reflects sound onto a region of the surface of the material M. The focusing apparatus 104 optionally includes an ellipsoidal sound reflector 302. For example, the sound generator 102 may produce an electrical spark 106 at one focus 304 of the ellipsoidal sound reflector 302 to generate the sound. The ellipsoidal sound reflector 302 optionally has an ellipsoidal reflector eccentricity of about 0-1. The ellipsoidal sound reflector 302 may have an ellipsoidal reflector depth of about 5-300 mm, and optionally has an ellipsoidal reflector minor axis of about 5-300 mm.

The sound produced optionally has an amplitude at the focus that is focused on a localized portion of the surface of the material M. The duration of the sound is optionally between about 0.5 microseconds and 1 millisecond. The frequency of the sound focused on the material M is optionally between about 1-100 kHz. The frequency of the sound focused on the material M may also be between about 100-500 kHz. The frequency of the sound focused on the material M is optionally between about 0.5-2.0 MHz. The example method may be performed on material M, including a porous aggregate, concrete, and metal.

The example method may further include the repetition of generating sound, and transmitting the generated sound. The repetition in the example methods is shown on FIG. 5 by the dotted line. Furthermore, the example method may include the repetition of coupling the transmitted sound through air into a material M to generate wave motion within the material. Also, the example method may further include receiving sound from the material M resulting from the wave motion to evaluate the material M. The received sound from a plurality of generation and transmission events may be averaged to evaluate the material M.

Figure 4:
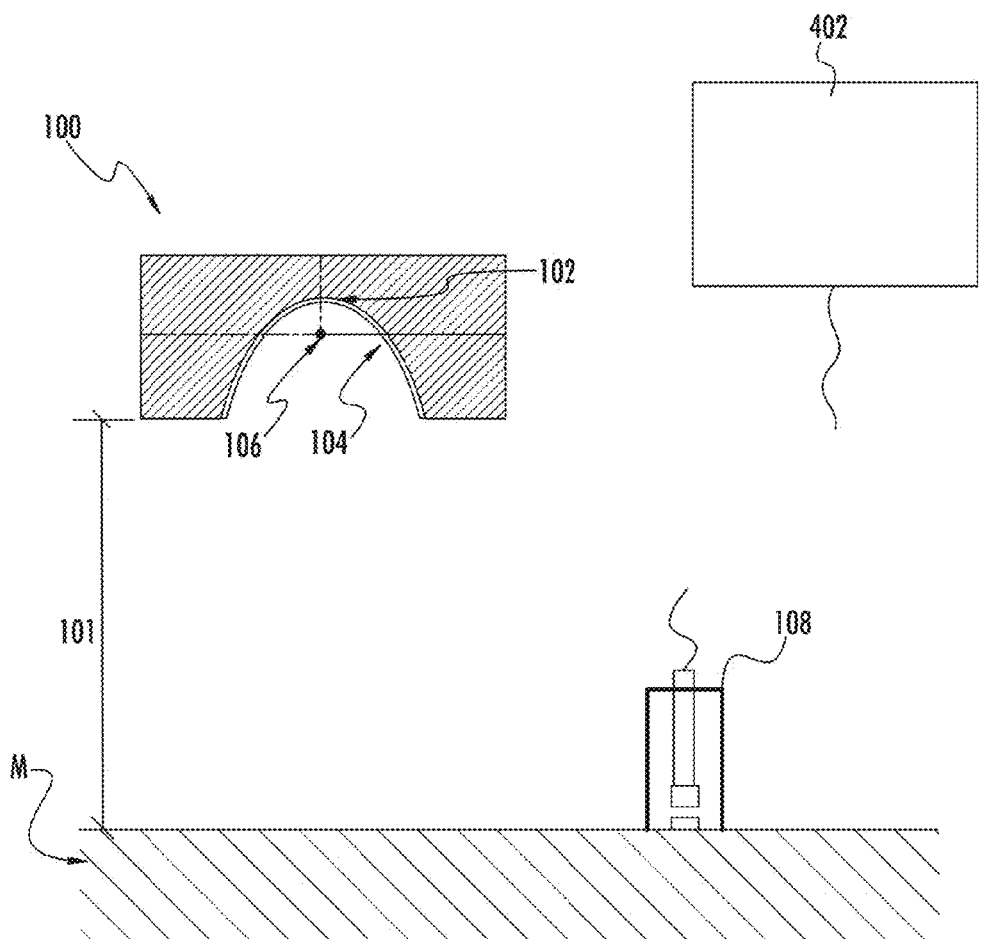
FIG. 4 is a schematic illustration showing an example system for non-destructive testing of a material.

Also provided herein is a system for non-destructive testing of a material M. Referring to FIG. 4, an example system for non-destructive testing of a material is shown. The system includes an acoustic source 100 and a receiver 108 for receiving sound produced from the wave motion of the material M. For example, the receiver may optionally be spaced from the source 100 and spaced from the material M. The receiver 108 is optionally a microphone. The system may further include at least one processor configured to process the received sound to evaluate the material.

Thus the methods, devices and systems described herein can optionally be implemented via a processing system 402 such as a general-purpose computing device in the form of a computer. The components of the computer can include, but are not limited to, one or more processors or processing units, a system memory, and a system bus that couples various system components including the processor to the system memory.

The system bus may represent one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. The bus, and all buses specified in this description, can also be implemented over a wired or wireless network connection and each of the subsystems, including the processor, a mass storage device, an operating system, application software, data, a network adapter, system memory, an Input/Output Interface, a display adapter, a display device, and a human machine interface, can be contained within one or more remote computing devices at physically separate locations, connected through buses of this form, in effect implementing a fully distributed system.

The computer typically includes a variety of computer readable media. Such media can be any available media that is accessible by the computer and includes both volatile and non-volatile media, removable and non-removable media. The system memory includes computer readable media in the form of volatile memory, such as random access memory (RAM), and/or non-volatile memory, such as read only memory (ROM). The system memory typically contains data such as data and/or program modules such as operating system and application software that are immediately accessible to and/or are presently operated on by the processing unit. The computer may also include other removable/non-removable, volatile/non-volatile computer storage media. A mass storage device can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device, including by way of example, an operating system and application software. Each of the operating system and application software (or some combination thereof) may include elements of the programming and the application software. Data can also be stored on the mass storage device. Data can be stored in any of one or more databases known in the art. Examples of such databases include, DB2®, Microsoft® Access, Microsoft® SQL Server, Oracle®, mySQL, PostgreSQL, and the like. The databases can be centralized or distributed across multiple systems. Application software may include instructions for determining and communicating the position of the model fetus in the system and for advancing the model fetus in the system.

A user can enter commands and information into the computer via an input device. Examples of such input devices include, but are not limited to, a keyboard, pointing device (e.g., a "mouse"), a microphone, a joystick, a serial port, a scanner, and the like. These and other input devices can be connected to the processing unit via a human machine interface that is coupled to the system bus, but may be connected by other interface and bus structures, such as a parallel port, game port, or a universal serial bus (USB).

The computer can operate in a networked environment using logical connections to one or more remote computing devices. By way of example, a remote computing device can be a personal computer, portable computer, a server, a router, a network computer, a peer device or other common network node, and so on. Logical connections between the computer and a remote computing device can be made via a local area network (LAN) and a general wide area network (WAN). Such network connections can be through a network adapter. A network adapter can be implemented in both wired and wireless environments. Such networking environments are commonplace in offices, enterprise-wide computer networks, intranets, and the Internet.

An implementation of application software may be stored on or transmitted across some form of computer readable media. Computer readable media can be any available media that can be accessed by a computer. By way of example, and not limitation, computer readable media may comprise "computer storage media" and "communications media." "Computer storage media" include volatile and non-volatile, removable and non-removable media implemented in any method or technology for storage of information such as computer readable instructions, data structures, program modules, or other data.

Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer. An implementation of the disclosed method may be stored on or transmitted across some form of computer readable media.

The processing of the disclosed methods can be performed by software components. The disclosed methods may be described in the general context of computer-executable instructions, such as program modules, being executed by one or more computers or other devices. Generally, program modules include computer code, routines, programs, objects, components, data structures, etc. that perform particular tasks or implement particular abstract data types. The disclosed method may also be practiced in grid-based and distributed computing environments where tasks are performed by remote processing devices that are linked through a communications network. In a distributed computing environment, program modules may be located in both local and remote computer storage media including memory storage devices.

For example, the processing of the sound includes evaluation of whether the material is damaged or has mechanical property changes. The system for non-destructive testing of a material M may optionally be portable, and all components of the system may be adapted to a size and shape for portability. Thus, compared to currently available devices and systems, the present disclosure may be smaller and easier to carry, and the cost of system is much less than current devices and systems.

Figure 6:
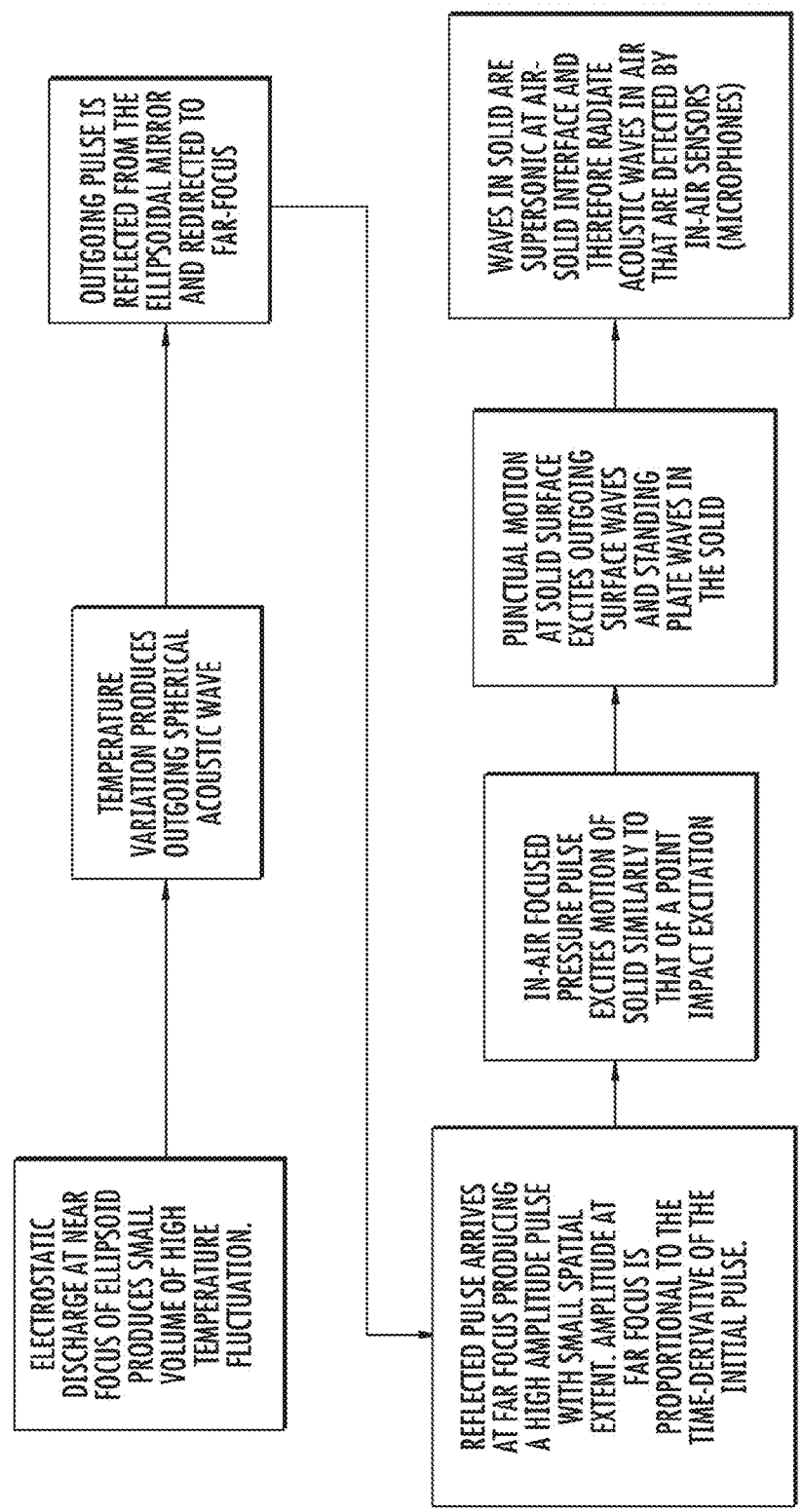
FIG. 6 is a flowchart showing an example measurement process using an acoustic source.

Referring now to FIG. 6, a flowchart for an example measurement process is shown. Electrostatic discharge at near focus 304 of the ellipsoidal reflector 302 may produce a small volume of high temperature fluctuations. The temperature variation may thereby produce outgoing spherical acoustic waves. The outgoing pulse is then optionally reflected from the ellipsoidal mirror and redirected to the far focus 306. The reflected pulse may arrive at far focus 306 and may produce a high amplitude pulse with small spatial extent. The amplitude at the far focus 306 may be proportional to the time-derivative of the initial pulse. The in-air focused pressure pulse optionally excites the motion of the solid similarly to that of a point impact excitation. Punctual motion at the solid surface may excite the outgoing surface waves and standing plate waves in the solid. The waves in the solid may be supersonic at the air-solid interface. Thus, the waves in the solid may radiate acoustic waves in air that are detected by in-air sensors, such as for example microphones.

EXAMPLES

Example 1

Air-Coupled Spectral Analysis of Surface Waves

Air-coupled Spectral Analysis of Surface Waves (SASW) tests were performed on full-scale concrete pavement.

Figure 8:
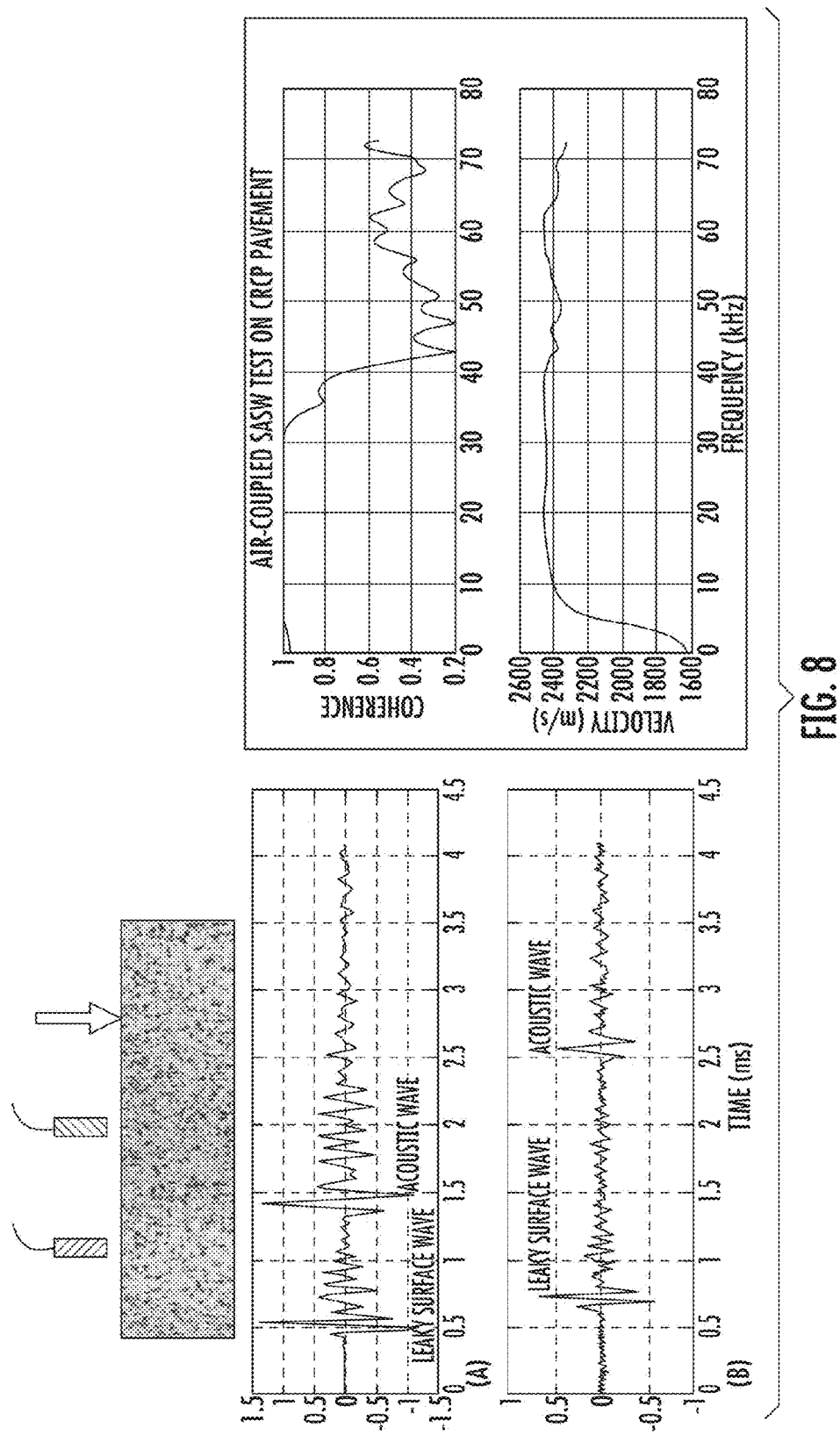
FIG. 8 shows an example setup and test results for air-coupled Spectral Analysis of Surface Waves.

Referring now to FIG. 8, an example setup and results are shown. These tests demonstrated signals with good coherence through 30 kHz.

Example 2

Air-Coupled Impact-Echo Tests

Figure 9:
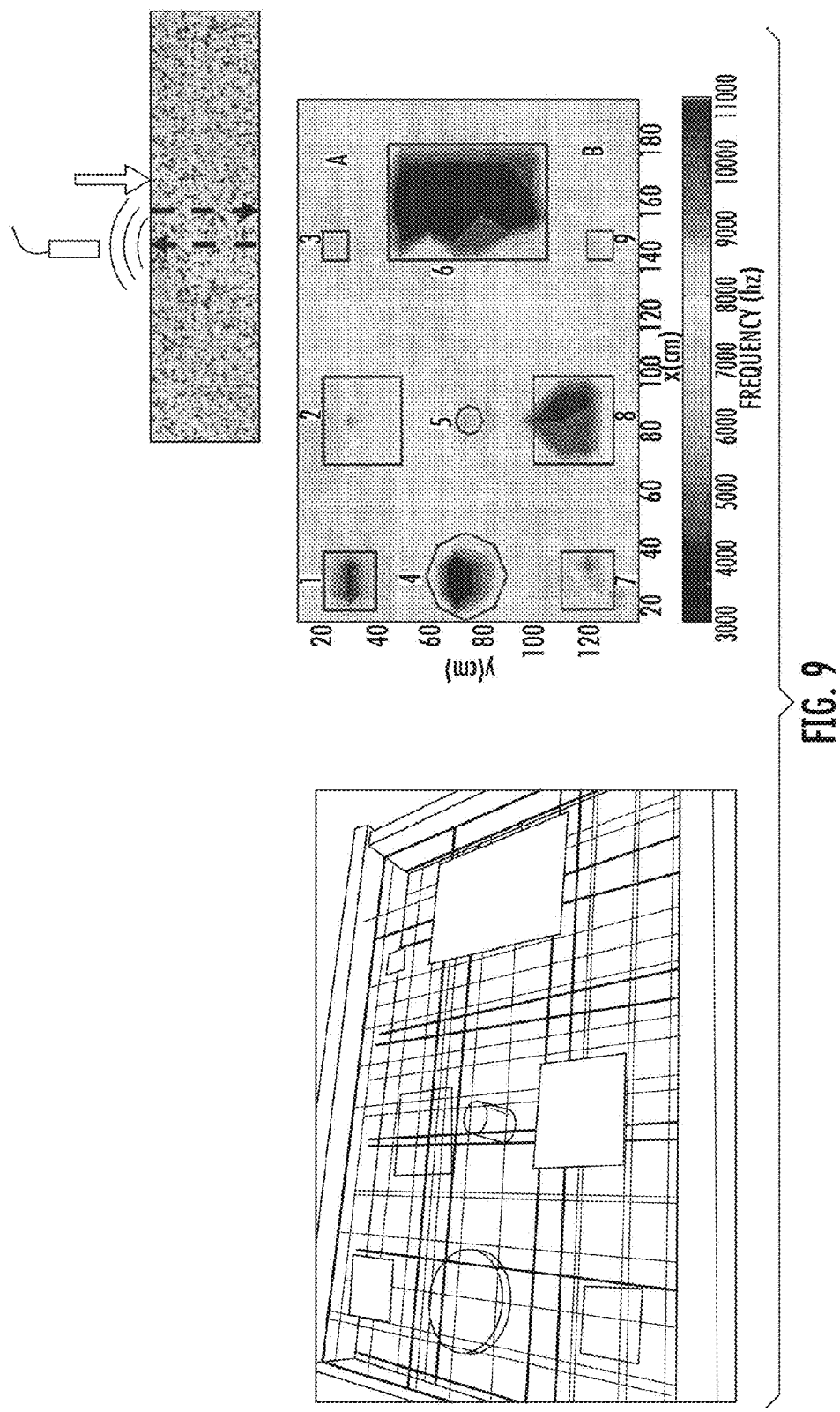
FIG. 9 shows an example setup and test results for air-coupled impact echo tests.

Tests showed the feasibility of an air-coupled impact-echo test by using a microphone as the receiver. Referring to FIG. 9, the setup is shown, as well as test results obtained from the air-coupled impact-echo test. Shallow delaminations were detected by using this test.

Example 3

Characterization of the Spark Source

Figure 10B:
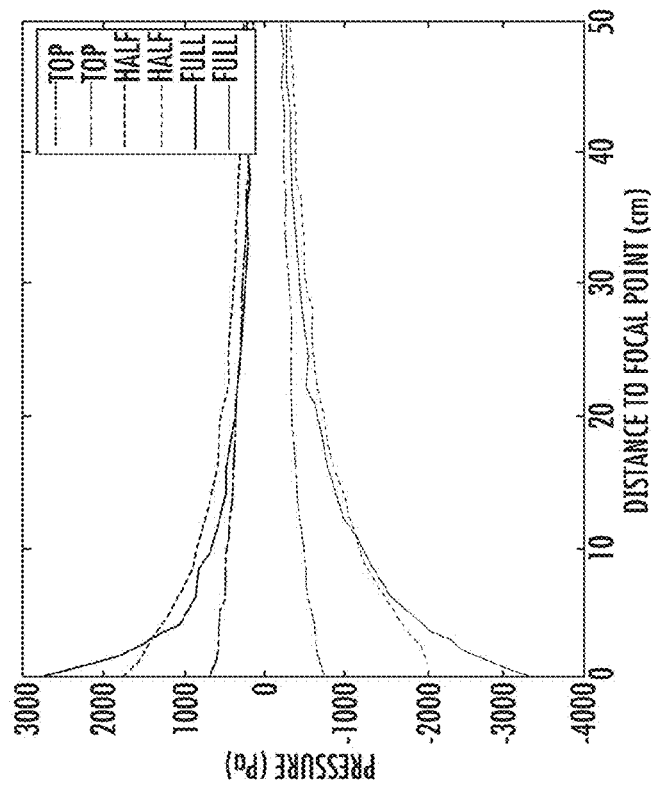
FIGS. 10A and 10B are graphs showing the results from tests measuring the peak and root mean square amplitudes at various distances from the focal point of the acoustic source.
Figure 10A:
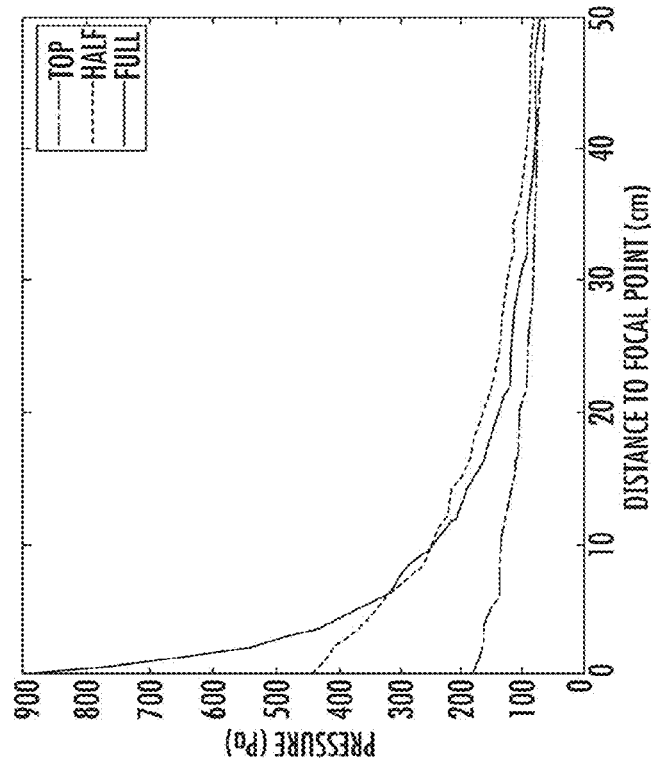

The peak and root mean square amplitudes were measured at various distances from the focal point of the acoustic source. The results are shown in FIGS. 10A and 10B. The largest excitation was determined to be at the focal point.

Example 4

Effect of Excitation Voltage

Figure 11A:
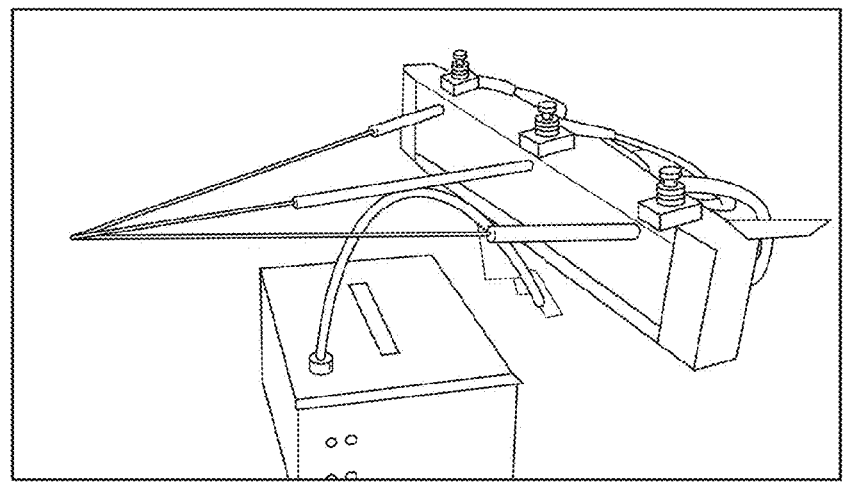
FIG. 11A is a schematic illustration of an example setup for determining the effect of excitation voltage.
Figure 11B:
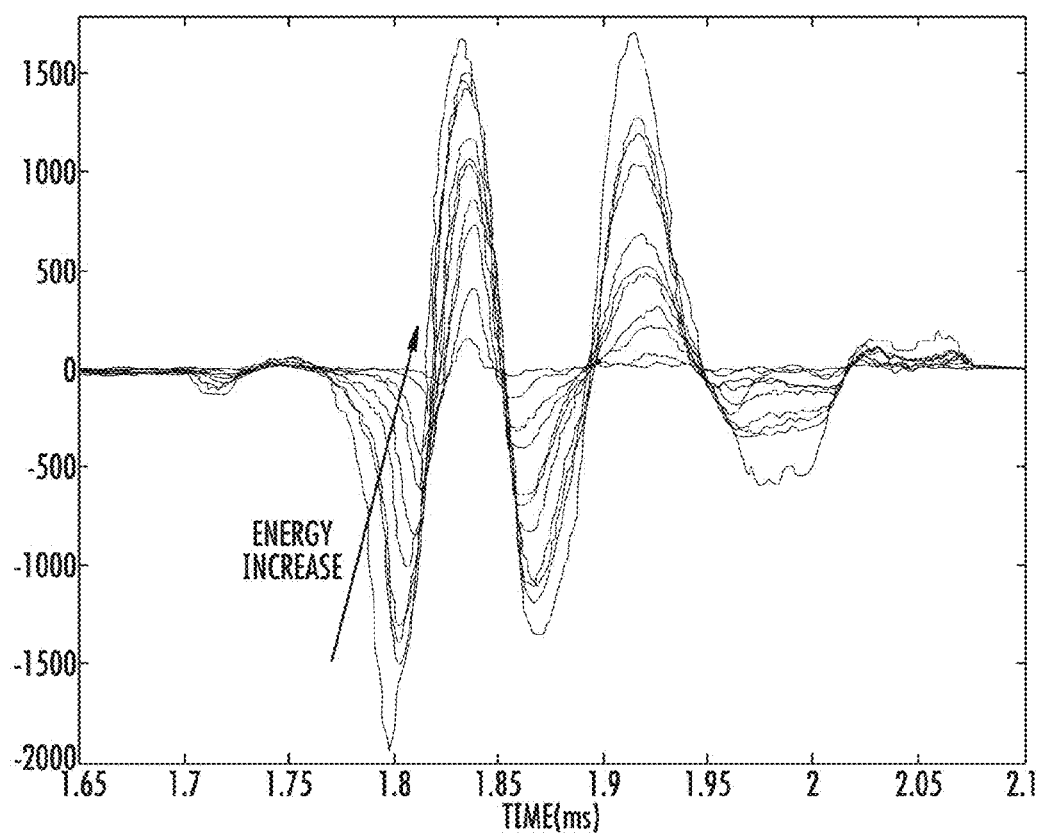
FIG. 11B is a graph showing the results from a test to determine the effect of excitation voltage.
Figure 12A:
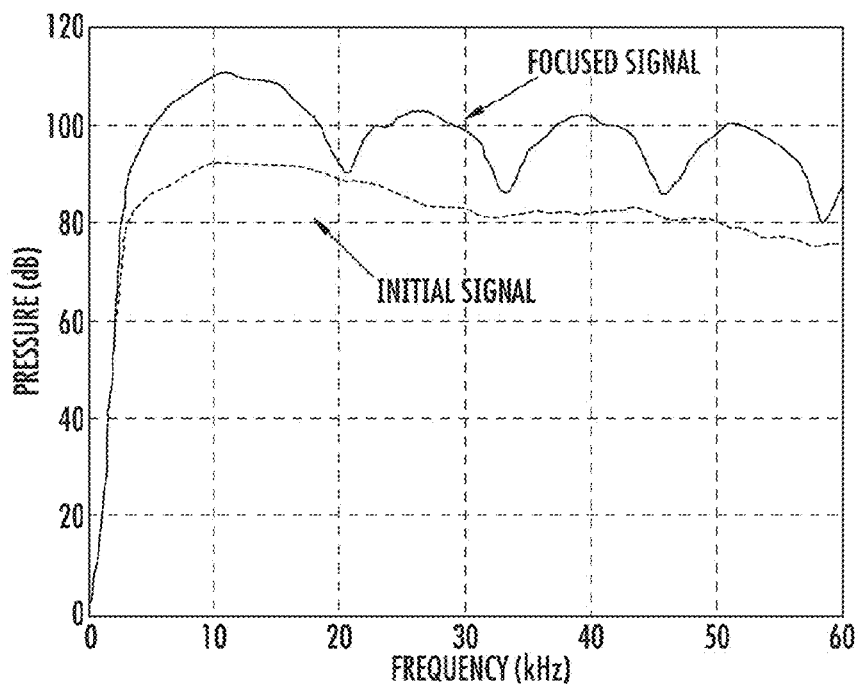
FIGS. 12A and 12B are graphs showing measured bandwidth of a spark source.
Figure 12B:
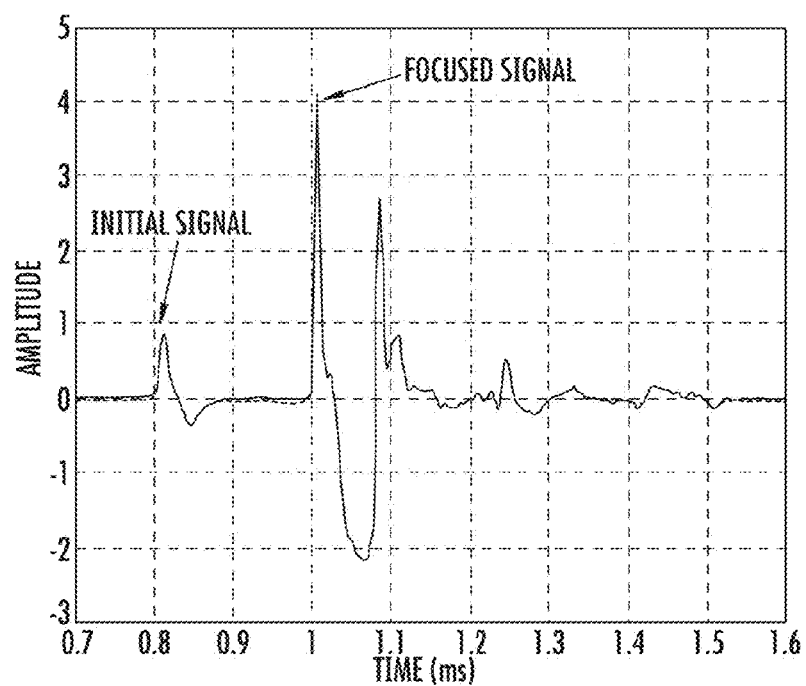

Tests to determine the effect of excitation voltage were performed. Referring now to FIG. 11A, an example setup is shown. FIG. 11B shows the test results. The test results demonstrated that the amplitude of the spark source can be controlled by excitation energy and electrode spacing. As shown in FIGS. 12A and 12B, test results showed that the spark source can have a broad bandwidth.

Example 5

Spark Source with Full Depth Reflector

Figure 13A:
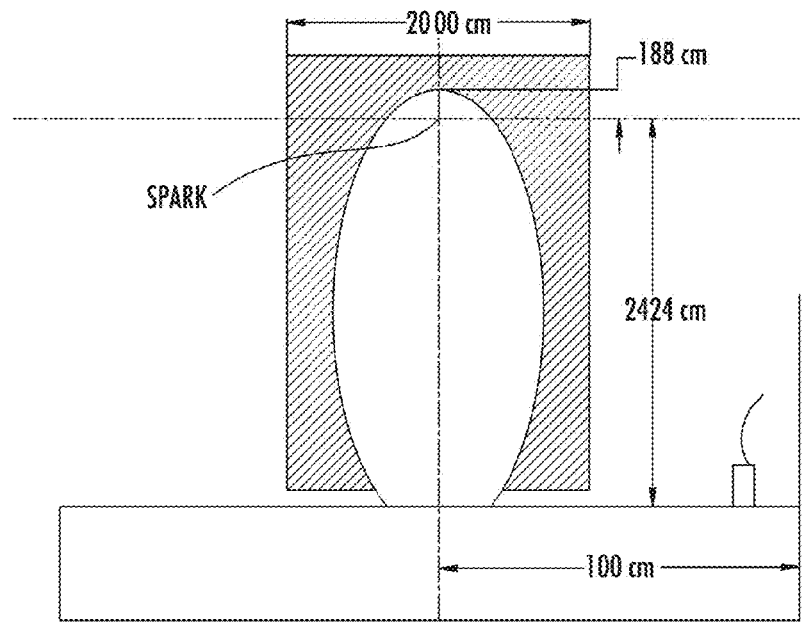
FIG. 13A is a schematic illustration of an example setup for a test using a spark source with a full depth reflector.
Figure 13B:
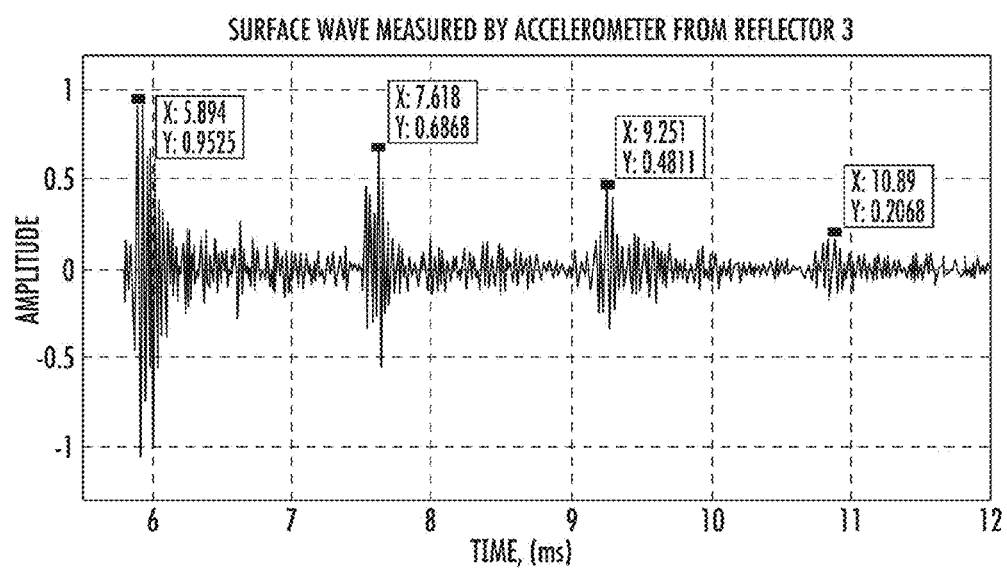
FIG. 13B is a graph showing the results from a test using a spark source with a full depth reflector.

Tests were performed using a spark source with a full depth reflector. Referring to FIG. 13A, an example setup is shown. The test was performed using multiple excitations in concrete by a single spark with a full depth reflector. The excitation interval used in the tests was 1.6 milliseconds. FIG. 13B shows the amplitude of the surface waves produced at various points in time. The test revealed that multiple excitations in concrete by a single spark with a full depth reflector allowed for signal averaging.

Example 6

Fully Air-Coupled Impact-Echo Tests

Figure 14A:
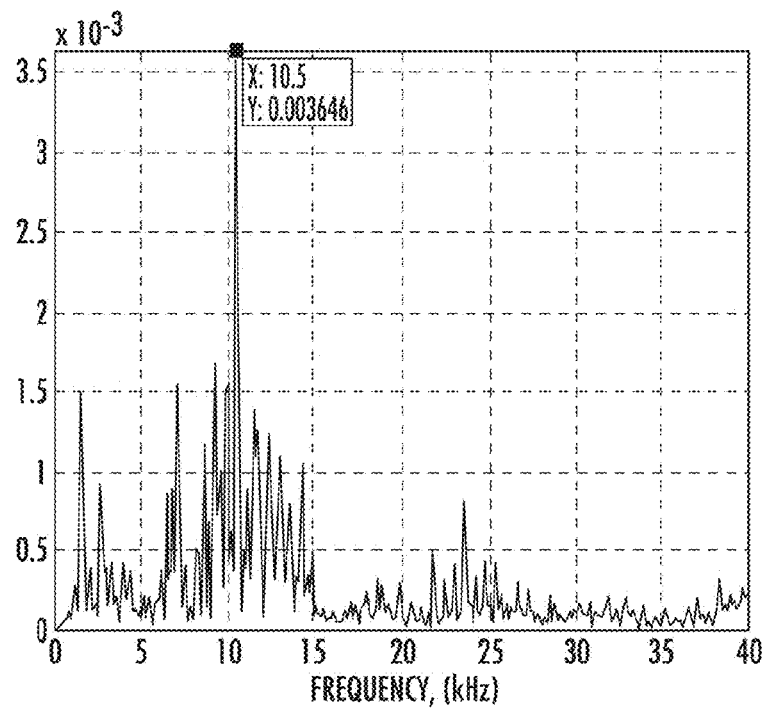
FIGS. 14A and 14B are graphs showing the results from fully air-coupled impact-echo test conducted on concrete slabs of varying thicknesses.
Figure 14B:
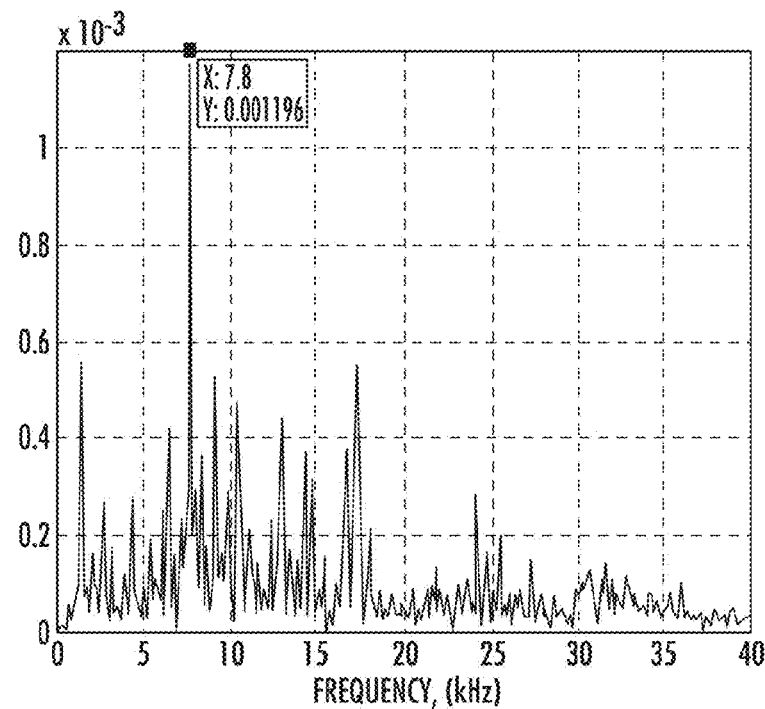

Fully air-coupled impact-echo tests were conducted using concrete slabs of varying thicknesses. Referring to FIG. 14A, the test results for a 190 mm thick concrete slab are shown. FIG. 14B shows the test results for a 254 mm concrete slab.

Example 7

Impact-Echo Test Using Spark Source on Shallow Delaminations

Figure 15A:
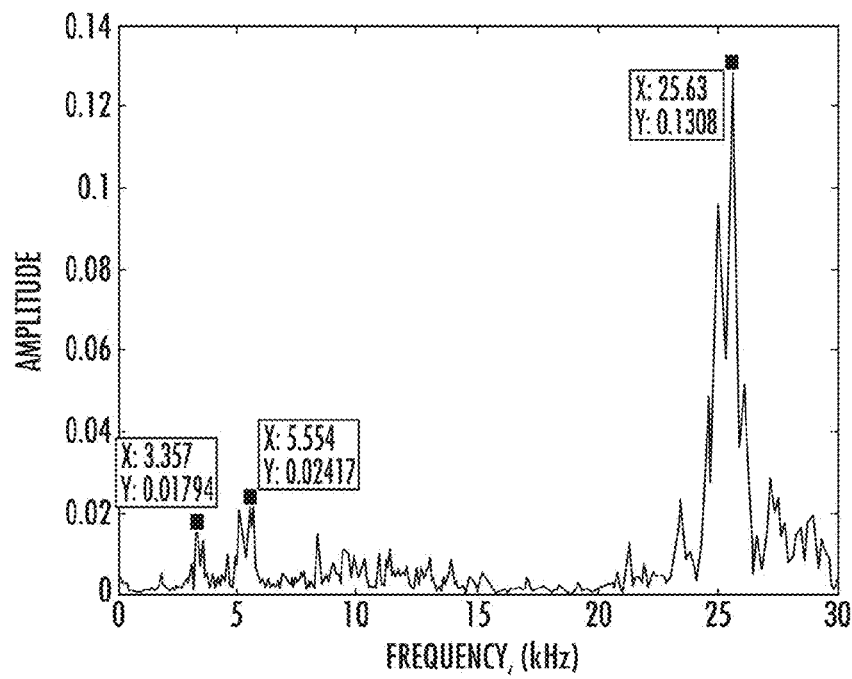
FIGS. 15A and 15B are graphs showing results from impact-echo tests using a spark source on a shallow delamination.
Figure 15B:
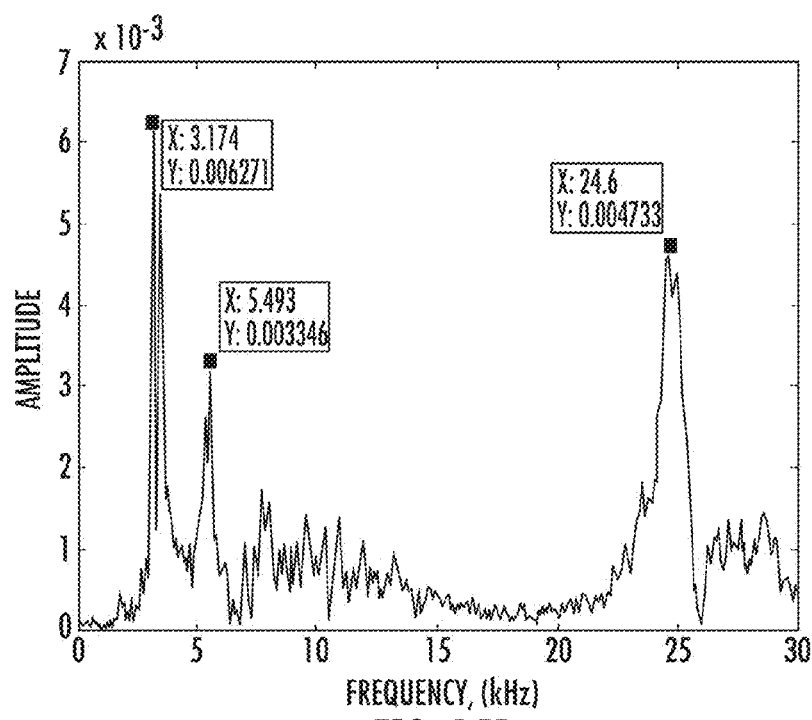

Impact-echo tests using a spark source on shallow delaminations were conducted. The receiver in these tests was an accelerometer. The tests were conducted on a concrete slab with a thickness of 254 mm, and a shallow delamination about 85 mm below the surface of the concrete slab. Referring to FIG. 15A, the test results using a spark source are shown. FIG. 15B shows the test results using an impact source, in which contact with the surface of the concrete was made. The impact-echo frequency was measured at 25.6 kHz, and was calculated to be 25.4 kHz. There were two flexural modes at 3.2 kHz and 5.5 kHz.

Example 8

Surface Wave Measurements Using a Spark Source

Figure 16A:
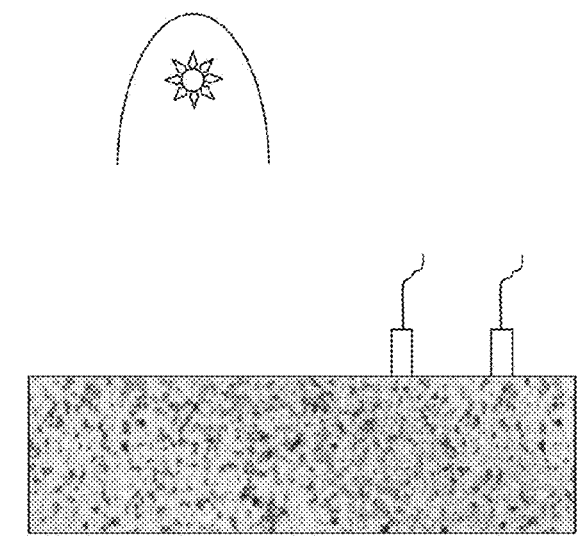
FIG. 16A is a schematic illustration of an example setup for a test using an air-coupled spark source to excite surface waves.
Figure 16B:
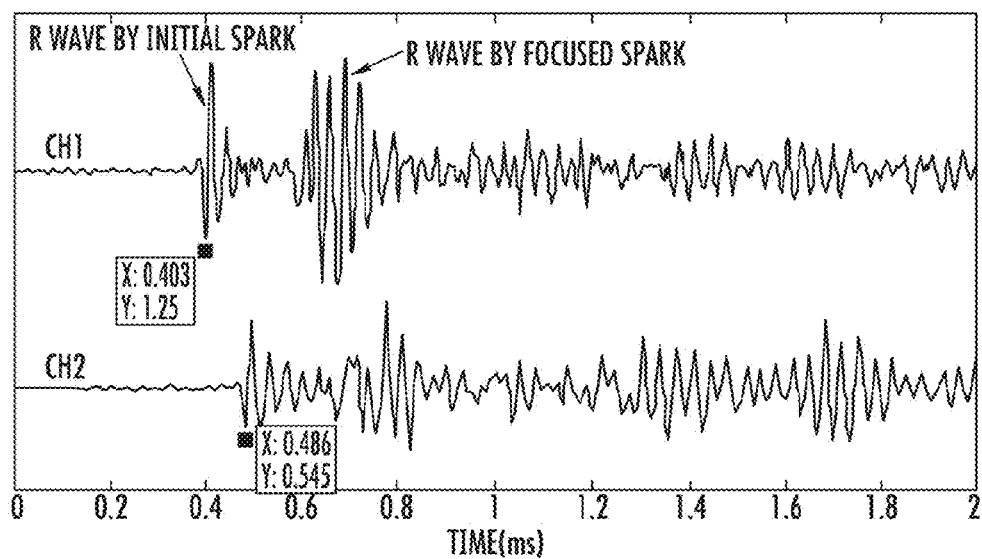
FIG. 16B is a graph showing results from a test using an air-coupled spark source to excite surface waves.

An air-coupled spark source was used to excite surface waves, and the surface waves of a material were measured by an accelerometer. The material used was a concrete slab that was 10 inches thick. Referring to FIG. 16A, an example setup for this test is shown, and FIG. 16B shows the test results obtained. The test revealed that the spark source was able to excite surface eaves in a 10-inch concrete slab.

Example 9

Fully Air-Coupled Surface Wave Measurements

Figure 17A:
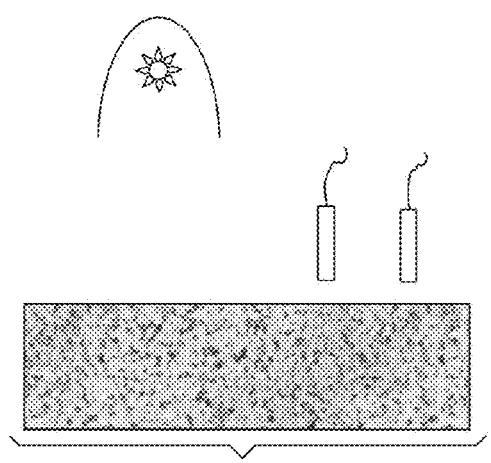
FIG. 17A is a schematic illustration of an example setup for fully air-coupled test using a spark source to measure the amplitude of surface waves.
Figure 17B:
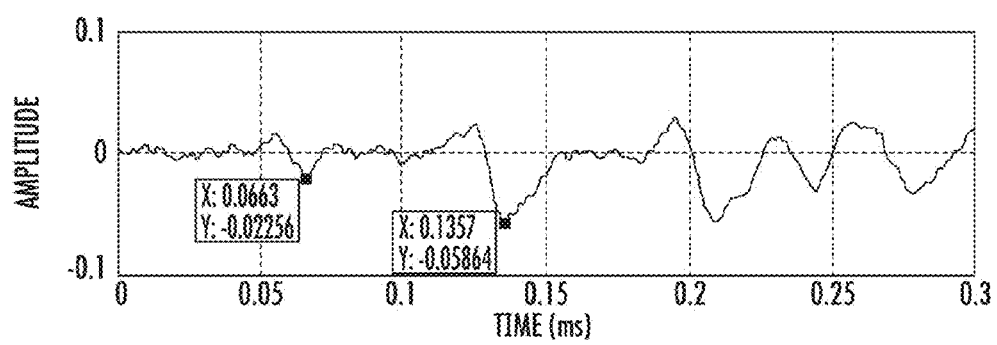
FIG. 17B is a graph showing results from a fully air-coupled test using a spark source to measure the amplitude of surface waves.
Figure 17B:
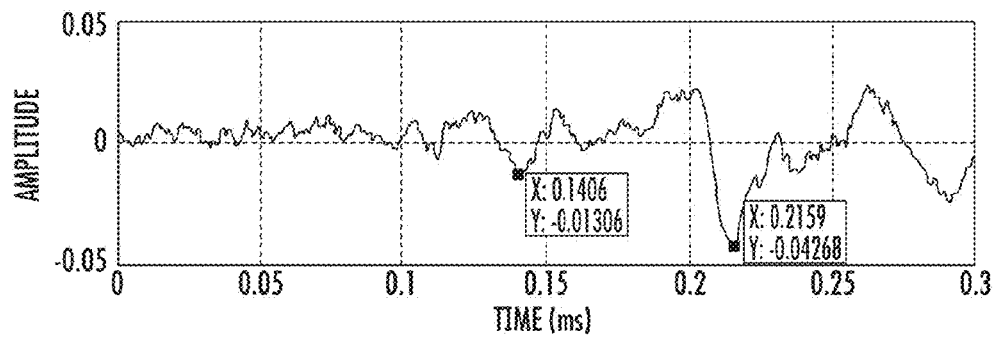

A spark source was used to conduct a fully air-coupled test and measure the amplitude of surface waves. The ellipsoidal reflector with a focal length of 121 mm was used, along with two microphones as receivers. An example setup is shown in FIG. 17A. The test results are shown in the charts in FIG. 17B.

Example 10

Fully Air-Coupled Test Using Through Transmission Setup

Figure 18A:
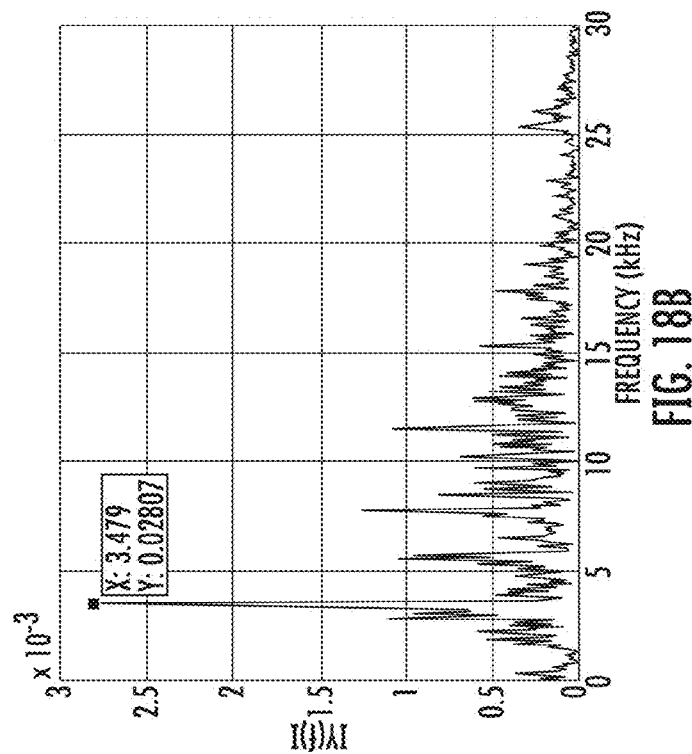
FIGS. 18A and 18B are graphs showing results from through transmission tests using contact and spark sources on a shallow delamination.
Figure 18B:
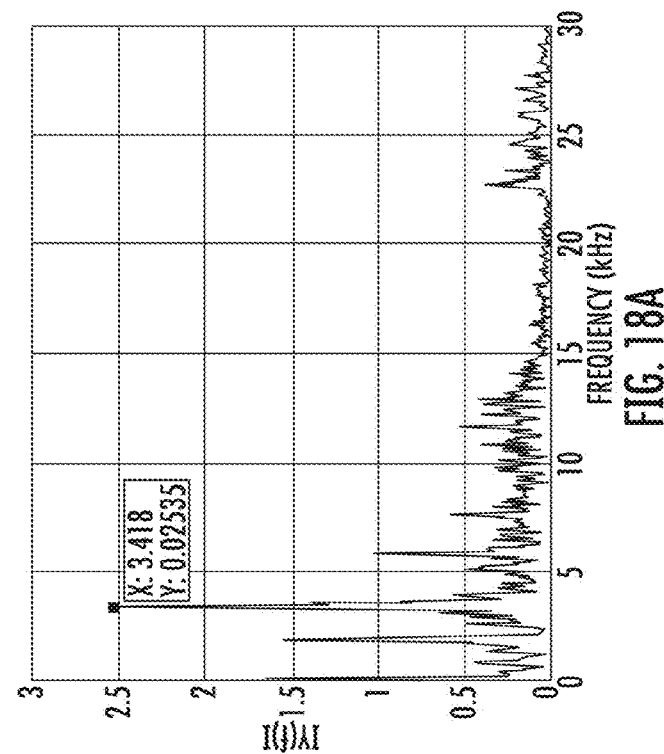

Fully air-coupled tests were conducted on a concrete slab using a through transmission setup, where the spark source and the microphone are placed on opposite sides of the concrete slab. In the through transmission test configuration, the test specimen serves as a sound barrier to block acoustic self-noise. The test results on a shallow delamination at a depth of 85 mm in a concrete slab are shown for the spark source and the contact source in FIGS. 18A and 18B, respectively. Both the contact source and the spark source resulted in the same resonant frequency of about 3.4 kHz, which corresponds to the flexural mode vibration of the delaminated concrete.

Example 11

Fully Air-Coupled Test on Steel Using Through Transmission Setup

Figure 19A:
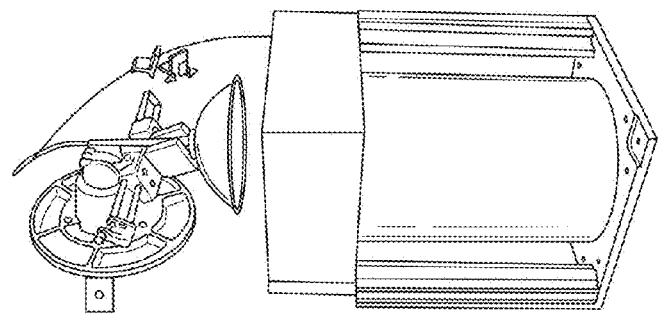
FIG. 19A is a schematic illustration of an example setup for fully air-coupled test using a through transmission test.
Figure 19B:
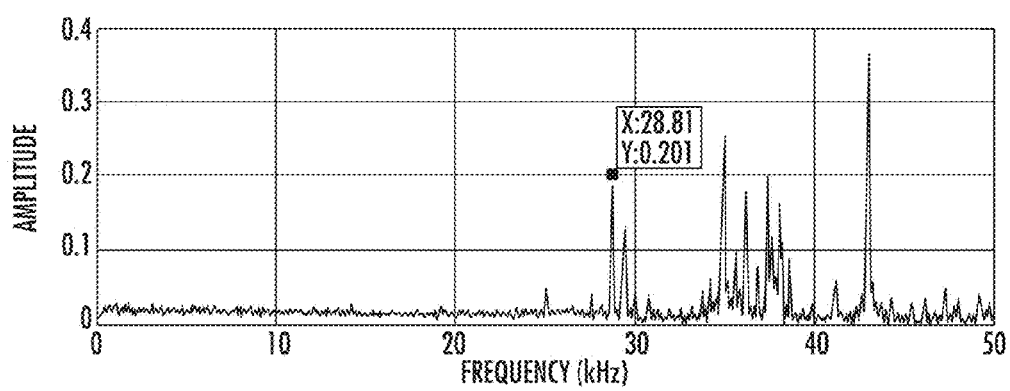
FIGS. 19B and 19C graphs showing results from through transmission tests using spark sources on a steel block and measured using a contact sensor and a microphone.
Figure 19C:
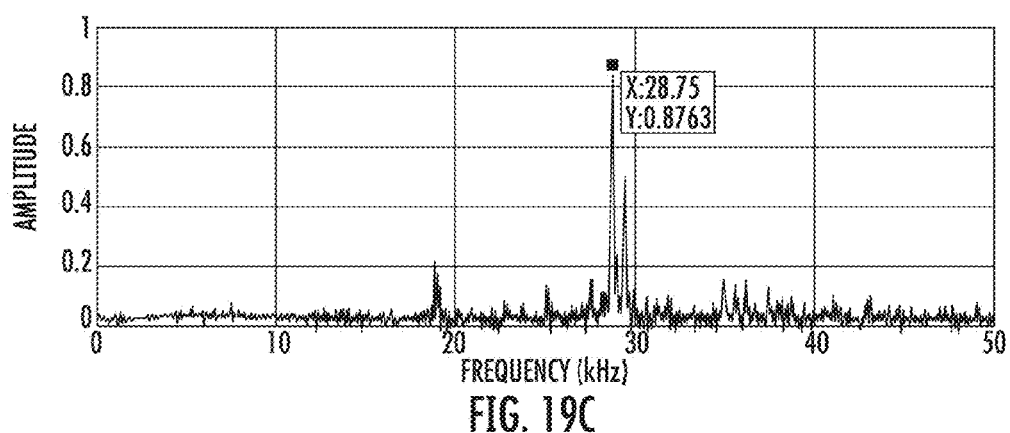

Fully air-coupled tests were conducted on a 102 mm (4-inch) thick steel block using a through transmission setup. Referring to FIG. 19A, an example setup using a spark source is shown. The test results for the signal spectra measured using a contact sensor and a microphone are shown in FIGS. 19B and 19C, respectively. Both the contact sensor and the microphone resulted in the same resonant frequency of about 28.8 Hz, which corresponds to the impact-echo mode vibration through the thickness of the steel block.

Many modifications and other embodiments of the disclosure set forth herein will come to mind to one skilled in the art to which this disclosure pertains having the benefit of the teachings presented in the foregoing description. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of non-destructive testing of a material, comprising:
   a. generating sound;
   b. transmitting the generated sound;
   c. coupling the transmitted sound through air into a material to generate wave motion within the material; and
   d. receiving sound from the material resulting from the wave motion to non-destructively evaluate the material;
   wherein:
      the sound is produced by a sound generator that produces an electrical spark which generates the sound;
      the sound generator comprises two electrodes spaced from one another by a predetermined gap distance; and
      a discharge voltage of the electrical spark is between 1 and 30 kV.

2. The method of claim 1, wherein the coupled sound penetrates into the material to a depth of about 1-25 mm.

3. The method of claim 2, wherein the coupled sound penetrates into the material to a depth of about 25-250 mm.

4. The method of claim 2, wherein the coupled sound penetrates into the material to a depth of about 250-625 mm.

5. The method of claim 1, further comprising focusing the sound onto the surface of the material.

6. The method of claim 5, wherein the focusing is accomplished with the use of a focusing apparatus that reflects sound onto a region of the surface of the material.

7. The method of claim 6, wherein the focusing apparatus comprises an ellipsoidal sound reflector.

8. The method of claim 7, wherein the sound generator produces an electrical spark at one focus of the ellipsoidal sound reflector to generate the sound.

9. The method of claim 7, wherein the ellipsoidal sound reflector has an ellipsoidal reflector eccentricity of about 0-1.

10. The method of claim 7, wherein the ellipsoidal sound reflector has an ellipsoidal reflector depth of about 5-300 mm.

11. The method of claim 7, wherein the ellipsoidal sound reflector has an ellipsoidal reflector minor axis of about 5-300 mm.

12. The method of claim 5, wherein the sound produced has an amplitude at the focus that is focused on a localized portion of the surface of the material.

13. The method of claim 1, wherein the sound has energy in frequencies sufficient for excitation of wave motion in the material.

14. The method of claim 1, wherein the sound has a power sufficient to penetrate into the material.

15. The method of claim 1, wherein a spark is generated between the two electrodes to produce sound.

16. The method of claim 1, wherein the gap distance is between about 0.1 mm and 10 mm.

17. The method of claim 1, wherein the duration of the sound is about 0.5 microseconds and 1 millisecond.

18. The source of claim 1, wherein the frequency of the sound focused on the material is between about 1-100 kHz.

19. The source of claim 1, wherein the frequency of the sound focused on the material is between about 100-500 kHz.

20. The source of claim 1, wherein the frequency of the sound focused on the material is between about 0.5-2.0 MHz.

21. The method of claim 1, wherein the frequency of the sound focused on the material is about 10-100 kHz.

22. The method of claim 1, wherein the material is selected from the group consisting of a porous aggregate, concrete and metal.

23. The method of claim 1, further comprising repeating:
   a. generating sound;
   b. transmitting the generated sound;
   c. coupling the transmitted sound through air into a material to generate wave motion within the material; and
   d. receiving sound from the material resulting from the wave motion to non-destructively evaluate the material.

24. The method of claim 23, wherein received sound from a plurality of generation and transmission events is averaged to evaluate the material.

25. A system for non-destructive testing of a material, comprising:
   a. an acoustic source, the acoustic source comprising:
      a sound generator comprising two electrodes spaced from one another by a predetermined gap distance, the sound generator producing an electrical spark which generates the sound; and
      a focusing apparatus that focuses sound generated by the sound generator through air onto a surface of a material to create wave motion within the material;
   b. a receiver for receiving sound produced from the wave motion of the material;
   wherein a discharge voltage of the electrical spark is between 1 and 30 kV.

26. The system of claim 25, wherein the receiver is spaced from the source and spaced from the material.

27. The system of claim 26, wherein the receiver is a microphone.

28. The system of claim 25, further comprising at least one processor configured to process the received sound to evaluate the material in a non-destructive manner.

29. The system of claim 28, wherein the processing of the sound includes evaluation of whether the material is damaged or has mechanical property changes.

30. The system of claim 25, wherein a spark is generated between the two electrodes to produce the sound.

31. The system of claim 25, wherein the gap distance is between about 0.1 mm and 10 mm.

32. The system of claim 25, wherein the focusing apparatus reflects sound produced by the sound generator.

33. The system of claim 32, wherein the focusing apparatus comprises an ellipsoidal sound reflector.

34. The system of claim 33, wherein sound generator produces an electrical spark at one focus of the ellipsoidal sound reflector to generate the sound.

35. The system of claim 33, wherein the ellipsoidal sound reflector has an ellipsoidal reflector eccentricity of about 0-1.

36. The system of claim 33, wherein the ellipsoidal sound reflector has an ellipsoidal reflector depth of about 5-300 mm.

37. The system of claim 33, wherein the ellipsoidal sound reflector has an ellipsoidal reflector minor axis of about 5-300 mm.

38. The system of claim 25, wherein the material is selected from the group consisting of a porous aggregate, concrete, metal, and composite material.

* * * * *